United States Patent
Wiltzius et al.

(10) Patent No.: US 10,844,120 B2
(45) Date of Patent: Nov. 24, 2020

(54) HUMANIZED ANTIGEN-BINDING DOMAINS AND METHODS OF USE

(71) Applicant: KITE PHARMA, INC., Santa Monica, CA (US)

(72) Inventors: Jed J. W. Wiltzius, Santa Monica, CA (US); Stuart A. Sievers, Santa Monica, CA (US)

(73) Assignee: Kite Pharma, Inc., Santa Monica, CA (US)

(*) Notice: Subject to any disclaimer, the term of this patent is extended or adjusted under 35 U.S.C. 154(b) by 121 days.

(21) Appl. No.: 15/961,562

(22) Filed: Apr. 24, 2018

(65) Prior Publication Data

US 2018/0312588 A1    Nov. 1, 2018

Related U.S. Application Data

(60) Provisional application No. 62/489,258, filed on Apr. 24, 2017.

(51) Int. Cl.
| | |
|---|---|
| C07K 16/28 | (2006.01) |
| A61K 39/395 | (2006.01) |
| A61P 35/00 | (2006.01) |
| A61K 35/17 | (2015.01) |
| A61P 35/02 | (2006.01) |
| C07K 14/725 | (2006.01) |
| A61K 39/00 | (2006.01) |

(52) U.S. Cl.
CPC .......... *C07K 16/2803* (2013.01); *A61K 35/17* (2013.01); *A61P 35/00* (2018.01); *A61P 35/02* (2018.01); *C07K 14/7051* (2013.01); *A61K 2039/505* (2013.01); *A61K 2039/572* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/92* (2013.01); *C07K 2317/94* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 5,091,513 | A | 2/1992 | Huston et al. |
| 5,132,405 | A | 7/1992 | Huston et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,728,388 | A | 3/1998 | Terman |
| 5,827,642 | A | 10/1998 | Riddell et al. |
| 5,830,462 | A | 11/1998 | Crabtree et al. |
| 5,834,266 | A | 11/1998 | Crabtree et al. |
| 5,869,337 | A | 2/1999 | Crabtree et al. |
| 6,040,177 | A | 3/2000 | Riddell et al. |
| 6,165,787 | A | 12/2000 | Crabtree et al. |
| 6,319,494 | B1 | 11/2001 | Capon et al. |
| 6,797,514 | B2 | 9/2004 | Berenson et al. |
| 6,867,041 | B2 | 3/2005 | Berenson et al. |
| 6,905,874 | B2 | 6/2005 | Berenson et al. |
| 7,709,226 | B2 | 5/2010 | Foote |
| 7,741,465 | B1 | 6/2010 | Eshar et al. |
| 8,486,693 | B2 | 7/2013 | Park et al. |
| 8,679,492 | B2 * | 3/2014 | Blein ................ C07K 16/2803 424/133.1 |
| 10,221,245 | B2 * | 3/2019 | Brogdon ........... C07K 16/2803 |
| 2002/0006409 | A1 | 1/2002 | Wood |
| 2011/0286980 | A1 | 11/2011 | Brenner |
| 2012/0130076 | A1 | 5/2012 | Holt et al. |
| 2013/0287748 | A1 | 10/2013 | June et al. |

(Continued)

FOREIGN PATENT DOCUMENTS

| | | |
|---|---|---|
| WO | 2008/081035 A1 | 7/2008 |
| WO | WO2010/095031 A2 | 8/2010 |

(Continued)

OTHER PUBLICATIONS

D. Sommermeyer et al., "Fully human CD19-specific chimeric antigen receptors for T-cell therapy", Leukemia 31(10): 2191-2199 (2017).
Al-Lazikani et al., "Standard conformations for the canonical structures of immunoglobulins" J Mol Biol 273: 927-948 (1997).
Baldwin et al. (eds.), "Monoclonal Antibodies for Cancer Detection and Therapy", pp. 303-216, Academic Press (1985).
Barbas et al., "Recombinant human Fab fragments neutralize human type 1 immunodeficiency virus in vitro", Proc. Natl. Acad. Sci. USA, 89(19): 9339-43 (1992).
Champe et al., "Monoclonal Antibodies That Block the Activity of Leukocyte Function-associated Antigen 1 Recognize Three Discrete Epitopes in the Inserted Domain of CD11a", J Biol Chem, 270(3): 1388-94 (1995).

(Continued)

*Primary Examiner* — Laura B Goddard
(74) *Attorney, Agent, or Firm* — Barnes & Thornburg LLP

(57) ABSTRACT

The invention provides a humanized anti-CD19 antibody or antigen binding fragment thereof comprising a light chain variable (VL) region and a heavy chain variable (VH) region in which the humanized VL and VL regions are derived from the mouse anti-CD19 clone FMC63 antibody; the humanized VL and/or humanized VH region comprise one or more amino acid substitutions in the framework region. The humanized anti-CD19 antibody or antigen binding fragment may be part of a single chain variable fragment (scFv), a chimeric antigen receptor (CAR) or a T cell receptor (TCR). Other aspects of the invention relate to cells comprising the CAR or the TCR and their use in a T cell therapy.

15 Claims, 18 Drawing Sheets
Specification includes a Sequence Listing.

(56) References Cited

U.S. PATENT DOCUMENTS

| | | |
|---|---|---|
| 2014/0050708 A1 | 2/2014 | Powell et al. |
| 2014/0099309 A1 | 4/2014 | Powell et al. |
| 2014/0154228 A1 | 6/2014 | Volk et al. |
| 2014/0171649 A1 | 6/2014 | Wang |
| 2014/0227237 A1 | 8/2014 | June et al. |
| 2014/0286987 A1 | 9/2014 | Spencer et al. |
| 2015/0266973 A1 | 9/2015 | Jarjour et al. |
| 2016/0046700 A1 | 2/2016 | Foster et al. |

FOREIGN PATENT DOCUMENTS

| | | |
|---|---|---|
| WO | 2012/033885 A1 | 3/2012 |
| WO | 2012/079000 A1 | 6/2012 |
| WO | 2012/129514 A1 | 9/2012 |
| WO | 2014/127261 A1 | 8/2014 |
| WO | WO2014/153270 A1 | 9/2014 |
| WO | 2014/186469 A2 | 11/2014 |
| WO | 2015/080981 A1 | 6/2015 |
| WO | 2015/090229 A1 | 6/2015 |
| WO | 2015/142675 A2 | 9/2015 |
| WO | 2016/044745 A1 | 3/2016 |
| WO | WO2016/033570 A1 | 3/2016 |
| WO | 2016/090369 A1 | 6/2016 |
| WO | WO2017/015783 A1 | 2/2017 |

OTHER PUBLICATIONS

Chayen, "The role of oil in macromolecular crystallization", Structure, 5(10): 1269-1274 (1997).
Cheung et al., "Epitope-specific antibody response to the surface antigen of duck hepatitis B virus in infected ducks", Virology, 176(2): 546-552 (1990).
Chothia et al., "Canonical structures for the hypervariable regions of immunoglobulins", J Mol Biol, 196: 901-917 (1987).
Chothia et al., "Structural repertoire of the human VH segments" J Mol Biol, 227: 799-817 (1992).
Cole et al., In: "Monoclonal Antibodies and Cancer Therapy", Alan R. Liss, Inc., pp. 77-96 (1985).
Cote et al., Generation of human monoclonal antibodies reactive with cellular antigens, Proc Natl Acad Sci USA, 80(7): 2026-2030 (1983).
Cunningham et al., "High-resolution epitope mapping of hGH-receptor interactions by alanine-scanning mutagenesis", Science, 244(4908): 1081-85 (1989).
Dayhoff et al., "Atlas of Protein Sequence and Structure: A Model of Evolutionary Change in Proteins", 5:345-352 (1978).
Devereux et al., "A comprehensive set of sequence analysis programs for the VAX", Nucl. Acid Res., 12: 387-395 (1984).
Eshhar et al., "Tumor-specific T-bodies: towards clinical application", Cancer Immunol Immunotherapy, 45(3-4): 11-31-136 (1997).
Fegan et al. "Chemically controlled protein assembly: techniques and applications", Chem. Rev., 110(6): 3315-3336 (2010).
Finney et al., "Chimeric receptors providing both primary and costimulatory signaling in T cells from a single gene product", Journal of Immunology, 161(6): 2791-2797 (1998).
Fishwild et al., "High-avidity human IgG kappa monoclonal antibodies from a novel strain of minilocus transgenic mice.", Nature Biotechnology, 14(7): 845 51 (1996).
Giege et al., "Crystallogenesis of biological macromolecules: facts and perspectives", Acta Crystallogr D Biol Crystallogr, 50(Pt 4): 339-350 (1994).
Gross et al., "Therapeutic Potential of T Cell Chimeric Antigen Receptors (CARs) in Cancer Treatment: Counteracting Off-Tumor Toxicities for Safe CAR T Cell Therapy", Annu. Rev. Pharmacol. Toxicol., 56: 59-83 (2016).
Hellstrom et al., "Antibodies for Drug Delivery", in Controlled Drug Delivery (2nd Ed.), Robinson et al. (eds.), Marcel Dekker, Inc., 623-53 (1987).
Henikoff et al., "Amino acid substitution matrices from protein blocks", Proc. Natl. Acad. Sci. U.S.A., 89(22): 10915-10919 (1992).

Hoogenboom et al., "By-passing immunisation. Human antibodies from synthetic repertoires of germline VH gene segments rearranged in vitro", J. Mol. Biol., 227(2): 381-8 (1991).
Huston et al., "Protein engineering of antibody binding sites: recovery of specific activity in an anti-digoxin single-chain Fv analogue produced in *Escherichia coli*", Proc Nat Acad Sci USA 85(16): 5879-5883 (1988).
Kabat et al., "Attempts to locate complementarity-determining residues in the variable positions of light and heavy chains", Ann NY Acad Sci, 190: 382-391 (1971).
Kalos et al., "T cells with chimeric antigen receptors have potent antitumor effects and can establish memory in patients with advanced leukemia", Sci. Transl. Med., 3(95): 95ra73 (2011).
Kirkland et al., "Analysis of the fine specificity and cross-reactivity of monoclonal anti-lipid A antibodies", J. Immunol. 137(11): 3614-3619 (1986).
Kozbor et al., "The production of monoclonal antibodies from human lymphocytes", Immunol Today, 4(3): 72-9 (1983).
Krause et al., "Antigen-dependent CD28 Signaling Selectively Enhances Survival and Proliferation in Genetically Modified Activated Human Primary T Lymphocytes", J. Exp. Med., 188(4): 619-626 (1998).
Lonberg et al., "Antigen-specific human antibodies from mice comprising four distinct genetic modifications", Nature, 368(6474): 856 859 (1994).
Lonberg, "Human antibodies from transgenic mice", Intern. Rev. Immunol., 13(1) 65 93 (1995).
Marks et al., "By-passing immunization: building high affinity human antibodies by chain shuffling", Bio/Technology, 10(7), 779 783 (1992).
Marks et al., "By-passing immunization. Human antibodies from V-gene libraries displayed on phage", J. Mol. Biol., 222(3):581-97 (1991).
McPherson, "Crystallization of Proteins from Polyethylene Glycol", J Biol Chem, 251(20): 6300-6303 (1976).
McPherson, "Current approaches to macromolecular crystallization", Eur J Biochem, 189: 1-23 (1990).
Moldenhauer et al., "Identity of HML-1 antigen on intestinal intraepithelial T cells and of B-ly7 antigen on hairy cell leukaemia", Scand. J. Immunol., 32(2): 77-82 (1990).
Morel et al., "Monoclonal antibodies to bovine serum albumin: affinity and specificity determinations", Molec. Immunol., 25(1): 7-15 (1988).
Morrison, "Success in specification", Nature, 368, 812 13 (1994).
Neuberger, "Generating high-avidity human Mabs in mice", Nature Biotechnology, 14: 826 (1996).
Pinchera et al. (eds.), "Analysis, Results, and Future Prospective of the Therapeutic Use of Radiolabeled Antibody in cancer Therapy", in Monoclonal Antibodies for Cancer Detection and Therapy, pp. 475-506 (1985).
Porter et al., "Chimeric antigen receptor-modified T cells in chronic lymphoid leukemia", N. Engl. J. Med., 365(8): 725-33 (2011).
Rosenberg et al., "Adoptive cell transfer as personalized immunotherapy for human cancer", Cancer Immunology and Immunotherapy, 348: 62-68 (2015).
Reisfeld et al. (eds.), "Monoclonal Antibodies and Cancer Therapy", pp. 243-256, Alan R. Liss, Inc. (1985).
Song et al., "CD27 costimulation augments the survival and antitumor activity of redirected human T cells in vivo", Blood, 119(3): 696-706 (2012).
Stahli et al., "Distinction of epitopes by monoclonal antibodies", Methods in Enzymology, 92: 242-253 (1983).
Thorpe et al., "The preparation and cytotoxic properties of antibody-toxin conjugates", Immunol. Rev., 62: 119-58 (1982).
Tramontano et al., "Framework residue 71 is a major determinant of the position and conformation of the second hypervariable region in the VH domains of immunoglobulins" J Mol Biol, 215(1): 175-82 (1990).
Wu et al., "Remote control of therapeutic T cells through a small molecule-gated chimeric receptor", Science, 350:6258 (2014).

(56) References Cited

OTHER PUBLICATIONS

Zebedee et al., "Human combinatorial antibody libraries to hepatitis B surface antigen", Proc. Natl. Acad. Sci. USA, 89(8): 3175-79 (1992).

* cited by examiner

SEQUENCE LISTING

```
<160> NUMBER OF SEQ ID NOS: 37

<210> SEQ ID NO 1
<211> LENGTH: 816
<212> TYPE: DNA
<213> ORGANISM: Artificial Sequence
<220> FEATURE:
<223> OTHER INFORMATION: Synthetic Polynucleotide

<400> SEQUENCE: 1
atggaatgga cctgggtgtt cctgttcctg ctgagcgtga cagccggcgt gcactctgac      60
atccaaatga cgcaaacgac ctcaagtctg tccgcgagcc tgggcgaccg tgttacgatt     120
agctgccgtg cttcacaaga tatcagtaaa tacctgaact ggtatcagca aaaaccggat     180
ggtaccgtta aactgctgat ctatcatacg tctcgtctgc acagtggcgt cccgtcccgc     240
tttagcggtt ctggcagtgg taccgattat tcactgacga tttcgaacct ggaacaggaa     300
gacatcgcga cctactttg ccagcaaggt aatacctgc cgtatacgtt cggcggtggc      360
accaaactgg aaatcaccgg ctccacgtca ggctcgggta aaccgggcag cggtgaaggc     420
tctaccaaag gtgaagtcaa actgcaggaa agcggtccgg gtctggtcgc accgagccaa     480
tctctgagtg tgacctgtac ggtgtcgggt gttagcctgc cggattacgg cgtgtcatgg     540
attcgtcagc cgccgcgtaa aggtctggaa tggctgggtg ttatctgggg ctcggaaacc     600
acgtattaca atagtgcact gaaatcccgt ctgaccatta tcaaagacaa ctccaaatca     660
caggttttcc tgaaaatgaa cagcctgcaa accgatgaca cggcgatcta ttactgcgcc     720
aaacattatt actatggtgg ctcttatgct atggattatt ggggtcaagg cacctcggtt     780
acggtctcgt cacatcatca tcatcatcat tgataa                              816
```

```
<210> SEQ ID NO 2
<211> LENGTH: 816
<212> TYPE: DNA
<213> ORGANISM: Artificial Sequence
<220> FEATURE:
<223> OTHER INFORMATION: Synthetic Polynucleotide
```

<400> SEQUENCE: 2

```
atggaatgga cctgggtgtt cctgttcctg ctgagcgtga cagccggcgt gcactctgac    60
atccaaatga cccagtcgcc gtcctttctg agcgcaagcg tcggtgaccg tgttacgatt   120
acctgccgtg ccagccaaga catctctaaa tacctgaact ggtatcagca aaaaccggat   180
caggcaccga aactgctgat caaacatacc tcacgtctgc actcgggtgt cccgagccgc   240
tttagtggtt ccggctcagg taccgatttt accttcacga ttagctctct gcagccggaa   300
gacatcgcca cgtattactg ccagcaaggt aatacccctgc cgtacacgtt cggccaaggt   360
accaaactgg aaatcaaagg ctcgacgagc ggctctggta aacccgggctc tggtgaaggc   420
agtaccaaag gtgaagtgca gctggttgaa agcggtggtg gtctggttca accgggtcgt   480
tccctgcgtc tgtcatgtac ggcgagtggt gtctccctgc cggactatgg cgtcctggg   540
gtgcgtcagc cgccgggtaa aggtctggaa tggattggtg tgatctgggg cagtgaaacc   600
acgtattaca actcggccct gaaaagccgt tttaccattt ctcgcgataa cagtaaaaat   660
acgctgtacc tgcagatgaa tagcctgcgc gcggaagaca ccgccgttta ctactgcgca   720
aaacattact actacggtgg cagctatgct atggactact ggggtcaggg cacgctggtt   780
acggtgtcgt cacatcatca tcatcatcat tgataa                             816
```

<210> SEQ ID NO 3
<211> LENGTH: 816
<212> TYPE: DNA
<213> ORGANISM: Artificial Sequence
<220> FEATURE:
<223> OTHER INFORMATION: Synthetic Polynucleotide

<400> SEQUENCE: 3

```
atggaatgga cctgggtgtt cctgttcctg ctgagcgtga cagccggcgt gcactctgat    60
attcaaatga cccagtcccc gtcctcsctg agtgcctccg tcggtgaccg tgttacgatt   120
acctgccgtg cgagccaaga catctctaaa tacctgaact ggtatcagca aaaaccggat   180
caggcaccga aactgctgat caaacatacc tcacgtctgc actcgggtgt gccgagccgc   240
tttagtggtt ccggctcagg taccgattac accctgacga tcagctctct gcagccggaa   300
gactttgcca cgtattactg ccagcaaggt aatacccctgc cgtatacgtt cggccaaggt   360
accaaactgg aaatcaaagg ctcgacgagc ggctctggta aacccgggctc tggtgaaggc   420
agtaccaaag gtgaagtgca gctggttgaa agcggtggtg gtctggttca accgggtcgt   480
tccctgcgtc tgtcatgtac ggcgagtggt gtctccctgc cggactatgg cgtgtcctgg   540
attcgtcagc cgccgggtaa aggcctggaa tggattggtg tcatctgggg cagtgaaacc   600
acgtattaca actcggccct gaaaagccgt ttcaccatct ctcgcgataa cagtaaaaat   660
acgctgtacc tgcagatgaa tagcctgcgc gcggaagaca ccgccgttta ctactgcgca   720
aaacattact actacggtgg cagctatgct atggattact ggggtcaagg cacgctggtc   780
accgtttcgt cacatcatca tcatcatcat tgataa                             816
```

<210> SEQ ID NO 4
<211> LENGTH: 650
<212> TYPE: DNA
<213> ORGANISM: Artificial Sequence
<220> FEATURE:
<223> OTHER INFORMATION: Synthetic Polynucleotide

<400> SEQUENCE: 4

-continued

```
atggaatgga cctgggtgtt cctgttcctg ctgagcgtga cagccggcgt gcactctgac      60
attcagatga cgcaaagtcc gagtccggtt caggcaccga ttttaccttc acgattagct     120
ctctgcaacc ggaagacatc gccacgtatt actgccagca aggcaatacc ctgccgtaca     180
cgttcggtca gggcaccaaa ctggaaatca aggttcgac gagcggttct ggcaaaccgg      240
gttctggcga aggtagtacc aaaggccagg tccaactgca ggaaagcggc cgggtctgg      300 tgaaaccgtc cggtaccctg tcactgacgt gtgcggtgag tggcgttttcc ctgccggact    360 atggtgtttc ctggattcgt caaccgccgg gcaaaggtct ggaatggatt ggcgtcatct     420
ggggtagtga aaccacgtat tacaactcgg ccctgaaaag ccgtgtgacc atctctcgcg     480
ataacagtaa aaatacgctg tacctgcaga tgaatagcct gcgcgcggaa gacaccgccg     540
tttactactg cgcaaaacat tactactacg gcggtagcta tgctatggat tactggggtc     600
aaggcacgct ggttacggtt tcctcgcatc atcatcatca tcactgataa                650
```

<210> SEQ ID NO 5
<211> LENGTH: 816
<212> TYPE: DNA
<213> ORGANISM: Artificial Sequence
<220> FEATURE:
<223> OTHER INFORMATION: Synthetic Polynucleotide

<400> SEQUENCE: 5

```
atggaatgga cctgggtgtt cctgttcctg ctgagcgtga cagccggcgt gcactctgac      60
attcagatga cacagagccc ttcttccctg agcgccagcg tcggagatag agtgaccatt     120
acttgtagag ccagccagga catttccaaa tacctgaact ggtatcagca gaagcccggg     180
aaagctgtga agctgctgat ctaccacacc tctcggctgc atagtggagt cccttcaaga     240
ttctcaggca gcgggtccgg aactgactat actctgacca tcagctccct gcagcctgag     300
gatattgcaa cctacttctg ccagcagggc aatacccctgc catatacatt tggcggggga     360
accaaactgg agattaaggg gtctacaagt ggctcaggga accaggaag cggcgaaggg     420 tccacaaagg gccaggtgca gctgcaggag tctggaccag gcctggtgaa gccctctgaa     480
actctgagtg tcacatgtac tgtgagcgga gtctccctgc ccgactacgg cgtgagttgg     540
atcaggcagc cccctgggaa aggactggag tggctgggcg tcatttgggg gagcgaaacc     600
acatactata actcagccct gaagagccgg ctgacaatct ccaaagacac ttctaagaat     660
caggtgtttc tgaaaatgtc tagtctgact gccgctgata ccgcaatcta ctattgcgcc     720
aagcactact attacggcgg ctcctatgct atggattatt ggggggcaggg gactctggtc     780 actgtctcaa gccatcatca tcatcatcat tgataa                              816
```

<210> SEQ ID NO 6
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 6

Met Glu Trp Thr Trp Val Phe Leu Phe Leu Leu Ser Val Thr Ala Gly
1               5                   10                  15

Val His Ser

<210> SEQ ID NO 7
<211> LENGTH: 18
<212> TYPE: PRT

```
<213> ORGANISM: Artificial Sequence
<220> FEATURE:
<223> OTHER INFORMATION: Synthetic Polypeptide

<400> SEQUENCE: 7

Gly Ser Thr Ser Gly Ser Gly Lys Pro Gly Ser Gly Glu Gly Ser Thr
1               5                   10                  15

Lys Gly

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 8

His His His His His His
1               5

<210> SEQ ID NO 9
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 9

Met Glu Trp Thr Trp Val Phe Leu Phe Leu Leu Ser Val Thr Ala Gly
1               5                   10                  15

Val His Ser Asp Ile Gln Met Thr Gln Thr Thr Ser Ser Leu Ser Ala
                20                  25                  30

Ser Leu Gly Asp Arg Val Thr Ile Ser Cys Arg Ala Ser Gln Asp Ile
            35                  40                  45

Ser Lys Tyr Leu Asn Trp Tyr Gln Gln Lys Pro Asp Gly Thr Val Lys
        50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Thr Gly Ser
        115                 120                 125

Thr Ser Gly Ser Gly Lys Pro Gly Ser Gly Glu Gly Ser Thr Lys Gly
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240
```

Lys His Tyr Tyr Tyr Gly Gly Ser Tyr Ala Met Asp Tyr Trp Gly Gln
                245                 250                 255

Gly Thr Ser Val Thr Val Ser Ser His His His His His His
        260                 265                 270

<210> SEQ ID NO 10
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 10

Met Glu Trp Thr Trp Val Phe Leu Phe Leu Leu Ser Val Thr Ala Gly
1               5                   10                  15

Val His Ser Asp Ile Gln Met Thr Gln Ser Pro Ser Phe Leu Ser Ala
            20                  25                  30

Ser Val Gly Asp Arg Val Thr Ile Thr Cys Arg Ala Ser Gln Asp Ile
        35                  40                  45

Ser Lys Tyr Leu Asn Trp Tyr Gln Gln Lys Pro Asp Gln Ala Pro Lys
    50                  55                  60

Leu Leu Ile Lys His Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Gly Asn Thr
            100                 105                 110

Leu Pro Tyr Thr Phe Gly Gln Gly Thr Lys Leu Glu Ile Lys Gly Ser
        115                 120                 125

Thr Ser Gly Ser Gly Lys Pro Gly Ser Gly Glu Gly Ser Thr Lys Gly
    130                 135                 140

Glu Val Gln Leu Val Glu Ser Gly Gly Gly Leu Val Gln Pro Gly Arg
145                 150                 155                 160

Ser Leu Arg Leu Ser Cys Thr Ala Ser Gly Val Ser Leu Pro Asp Tyr
                165                 170                 175

Gly Val Ser Trp Val Arg Gln Pro Pro Gly Lys Gly Leu Glu Trp Ile
            180                 185                 190

Gly Val Ile Trp Gly Ser Glu Thr Thr Tyr Tyr Asn Ser Ala Leu Lys
        195                 200                 205

Ser Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Leu Val Thr Val Ser Ser His His His His His His
        260                 265                 270

<210> SEQ ID NO 11
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 11

Asp Ile Gln Met Thr Gln Ser Pro Ser Phe Leu Ser Ala Ser Val Gly
1               5                   10                  15

```
Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Leu Glu Ile Lys
            100                 105
```

<210> SEQ ID NO 12
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 12

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Val Ser Leu Pro Asp Tyr
            20                  25                  30

Gly Val Ser Trp Val Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120
```

<210> SEQ ID NO 13
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 13

```
Met Glu Trp Thr Trp Val Phe Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Lys Tyr Leu Asn Trp Tyr Gln Gln Lys Pro Asp Gln Ala Pro Lys
    50                  55                  60

Leu Leu Ile Lys His Thr Ser Arg Leu His Ser Gly Val Pro Ser Arg
65                  70                  75                  80

Phe Ser Gly Ser Gly Ser Gly Thr Asp Tyr Thr Leu Thr Ile Ser Ser
```

```
                        85                  90                  95
Leu Gln Pro Glu Asp Phe Ala Thr Tyr Tyr Cys Gln Gln Gly Asn Thr
                100                 105                 110
Leu Pro Tyr Thr Phe Gly Gln Gly Thr Lys Leu Glu Ile Lys Gly Ser
            115                 120                 125
Thr Ser Gly Ser Gly Lys Pro Gly Ser Gly Glu Gly Ser Thr Lys Gly
        130                 135                 140
Glu Val Gln Leu Val Glu Ser Gly Gly Gly Leu Val Gln Pro Gly Arg
145                 150                 155                 160
Ser Leu Arg Leu Ser Cys Thr Ala Ser Gly Val Ser Leu Pro Asp Tyr
                165                 170                 175
Gly Val Ser Trp Ile Arg Gln Pro Pro Gly Lys Gly Leu Glu Trp Ile
            180                 185                 190
Gly Val Ile Trp Gly Ser Glu Thr Thr Tyr Tyr Asn Ser Ala Leu Lys
        195                 200                 205
Ser Arg Phe Thr Ile Ser Arg Asp Asn Ser Lys Asn Thr Leu Tyr Leu
    210                 215                 220
Gln Met Asn Ser Leu Arg Ala Glu Asp Thr Ala Val Tyr Tyr Cys Ala
225                 230                 235                 240
Lys His Tyr Tyr Tyr Gly Gly Ser Tyr Ala Met Asp Tyr Trp Gly Gln
                245                 250                 255
Gly Thr Leu Val Thr Val Ser Ser His His His His His His
            260                 265                 270

<210> SEQ ID NO 14
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 14

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Lys Tyr
            20                  25                  30
Leu Asn Trp Tyr Gln Gln Lys Pro Asp Gln Ala Pro Lys Leu Leu Ile
        35                  40                  45
Lys His Thr Ser Arg Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Gly Asn Thr Leu Pro Tyr
                85                  90                  95
Thr Phe Gly Gln Gly Thr Lys Leu Glu Ile Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 15

Glu Val Gln Leu Val Glu Ser Gly Gly Gly Leu Val Gln Pro Gly Arg
1               5                   10                  15
```

```
Ser Leu Arg Leu Ser Cys Thr Ala Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Asn Ser Ala Leu Lys
            50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
            115                 120

<210> SEQ ID NO 16
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 16

Met Glu Trp Thr Trp Val Phe Leu Phe Leu Leu Ser Val Thr Ala Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Arg Ala Ser Gln Asp Ile
            35                  40                  45

Ser Lys Tyr Leu Asn Trp Tyr Gln Gln Lys Pro Asp Gln Ala Pro Lys
            50                  55                  60

Leu Leu Ile Lys His Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
            85                  90                  95

Leu Gln Pro Glu Asp Ile Ala Thr Tyr Tyr Cys Gln Gln Gly Asn Thr
            100                 105                 110

Leu Pro Tyr Thr Phe Gly Gln Gly Thr Lys Leu Glu Ile Lys Gly Ser
            115                 120                 125

Thr Ser Gly Ser Gly Lys Pro Gly Ser Gly Glu Gly Ser Thr Lys Gly
            130                 135                 140

Gln Val Gln Leu Gln Glu Ser Gly Pro Gly Leu Val Lys Pro Ser Gly
145                 150                 155                 160

Thr Leu Ser Leu Thr Cys Ala Val Ser Gly Val Ser Leu Pro Asp Tyr
            165                 170                 175

Gly Val Ser Trp Ile Arg Gln Pro Pro Gly Lys Gly Leu Glu Trp Ile
            180                 185                 190

Gly Val Ile Trp Gly Ser Glu Thr Thr Tyr Tyr Asn Ser Ala Leu Lys
            195                 200                 205

Ser Arg Val Thr Ile Ser Arg Asp Asn Ser Lys Asn Thr Leu Tyr Leu
            210                 215                 220

Gln Met Asn Ser Leu Arg Ala Glu Asp Thr Ala Val Tyr Tyr Cys Ala
225                 230                 235                 240

Lys His Tyr Tyr Tyr Gly Gly Ser Tyr Ala Met Asp Tyr Trp Gly Gln
            245                 250                 255
```

```
Gly Thr Leu Val Thr Val Ser Ser His His His His His His
            260                 265                 270

<210> SEQ ID NO 17
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 18

Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 19
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 19

Met Glu Trp Thr Trp Val Phe Leu Phe Leu Leu Ser Val Thr Ala Gly
```

```
                1               5                  10                 15
            Val His Ser Asp Ile Gln Met Thr Gln Ser Pro Ser Ser Leu Ser Ala
                        20                  25                  30
            Ser Val Gly Asp Arg Val Thr Ile Thr Cys Arg Ala Ser Gln Asp Ile
                        35                  40                  45
            Ser Lys Tyr Leu Asn Trp Tyr Gln Gln Lys Pro Gly Lys Ala Val Lys
                50                  55                  60
            Leu Leu Ile Tyr His Thr Ser Arg Leu His Ser Gly Val Pro Ser Arg
            65                  70                  75                  80
            Phe Ser Gly Ser Gly Ser Gly Thr Asp Tyr Thr Leu Thr Ile Ser Ser
                            85                  90                  95
            Leu Gln Pro Glu Asp Ile Ala Thr Tyr Phe Cys Gln Gln Gly Asn Thr
                        100                 105                 110
            Leu Pro Tyr Thr Phe Gly Gly Gly Thr Lys Leu Glu Ile Lys Gly Ser
                        115                 120                 125
            Thr Ser Gly Ser Gly Lys Pro Gly Ser Gly Glu Gly Ser Thr Lys Gly
                        130                 135                 140
            Gln Val Gln Leu Gln Glu Ser Gly Pro Gly Leu Val Lys Pro Ser Glu
            145                 150                 155                 160
            Thr Leu Ser Val Thr Cys Thr Val Ser Gly Val Ser Leu Pro Asp Tyr
                                165                 170                 175
            Gly Val Ser Trp Ile Arg Gln Pro Pro Gly Lys Gly Leu Glu Trp Leu
                        180                 185                 190
            Gly Val Ile Trp Gly Ser Glu Thr Thr Tyr Tyr Asn Ser Ala Leu Lys
                        195                 200                 205
            Ser Arg Leu Thr Ile Ser Lys Asp Thr Ser Lys Asn Gln Val Phe Leu
                        210                 215                 220
            Lys Met Ser Ser Leu Thr Ala Ala Asp Thr Ala Ile Tyr Tyr Cys Ala
            225                 230                 235                 240
            Lys His Tyr Tyr Tyr Gly Gly Ser Tyr Ala Met Asp Tyr Trp Gly Gln
                                245                 250                 255
            Gly Thr Leu Val Thr Val Ser Ser His His His His His His
                        260                 265                 270

<210> SEQ ID NO 20
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
```

```
                100                 105
```

<210> SEQ ID NO 21
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 21

```
Gln Val Gln Leu Gln Glu Ser Gly Pro Gly Leu Val Lys Pro Ser Glu
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Phe Leu
65                  70                  75                  80

Lys Met Ser Ser Leu Thr Ala Ala Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120
```

<210> SEQ ID NO 22
<211> LENGTH: 264
<212> TYPE: PRT
<213> ORGANISM: Artificial Sequence
<220> FEATURE:
<223> OTHER INFORMATION: Synthetic Polypeptide

<400> SEQUENCE: 22

```
Met Glu Trp Thr Trp Val Phe Leu Phe Leu Leu Ser Val Thr Ala Gly
1               5                   10                  15

Val His Ser Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Lys Tyr Leu Asn Trp Tyr Gln Gln Lys Pro Asp Gly Thr Val Lys
    50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Thr Gly Ser
        115                 120                 125

Thr Ser Gly Ser Gly Lys Pro Gly Ser Gly Glu Gly Ser Thr Lys Gly
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175
```

```
Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser
            260
```

<210> SEQ ID NO 23
<211> LENGTH: 264
<212> TYPE: PRT
<213> ORGANISM: Artificial Sequence
<220> FEATURE:
<223> OTHER INFORMATION: Synthetic Polypeptide

<400> SEQUENCE: 23

```
Met Glu Trp Thr Trp Val Phe Leu Phe Leu Leu Ser Val Thr Ala Gly
1               5                   10                  15

Val His Ser Asp Ile Gln Met Thr Gln Ser Pro Ser Phe Leu Ser Ala
            20                  25                  30

Ser Val Gly Asp Arg Val Thr Ile Thr Cys Arg Ala Ser Gln Asp Ile
        35                  40                  45

Ser Lys Tyr Leu Asn Trp Tyr Gln Gln Lys Pro Asp Gln Ala Pro Lys
    50                  55                  60

Leu Leu Ile Lys His Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Gly Asn Thr
            100                 105                 110

Leu Pro Tyr Thr Phe Gly Gln Gly Thr Lys Leu Glu Ile Lys Gly Ser
        115                 120                 125

Thr Ser Gly Ser Gly Lys Pro Gly Ser Gly Glu Gly Ser Thr Lys Gly
    130                 135                 140

Glu Val Gln Leu Val Glu Ser Gly Gly Gly Leu Val Gln Pro Gly Arg
145                 150                 155                 160

Ser Leu Arg Leu Ser Cys Thr Ala Ser Gly Val Ser Leu Pro Asp Tyr
                165                 170                 175

Gly Val Ser Trp Val Arg Gln Pro Pro Gly Lys Gly Leu Glu Trp Ile
            180                 185                 190

Gly Val Ile Trp Gly Ser Glu Thr Thr Tyr Tyr Asn Ser Ala Leu Lys
        195                 200                 205

Ser Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Leu Val Thr Val Ser Ser
            260
```

<210> SEQ ID NO 24
<211> LENGTH: 264
<212> TYPE: PRT
<213> ORGANISM: Artificial Sequence
<220> FEATURE:
<223> OTHER INFORMATION: Synthetic Polypeptide

<400> SEQUENCE: 24

```
Met Glu Trp Thr Trp Val Phe Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Lys Tyr Leu Asn Trp Tyr Gln Gln Lys Pro Asp Gln Ala Pro Lys
    50                  55                  60

Leu Leu Ile Lys His Thr Ser Arg Leu His Ser Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Phe Ala Thr Tyr Tyr Cys Gln Gln Gly Asn Thr
            100                 105                 110

Leu Pro Tyr Thr Phe Gly Gln Gly Thr Lys Leu Glu Ile Lys Gly Ser
        115                 120                 125

Thr Ser Gly Ser Gly Lys Pro Gly Ser Gly Glu Gly Ser Thr Lys Gly
    130                 135                 140

Glu Val Gln Leu Val Glu Ser Gly Gly Gly Leu Val Gln Pro Gly Arg
145                 150                 155                 160

Ser Leu Arg Leu Ser Cys Thr Ala Ser Gly Val Ser Leu Pro Asp Tyr
                165                 170                 175

Gly Val Ser Trp Ile Arg Gln Pro Pro Gly Lys Gly Leu Glu Trp Ile
            180                 185                 190

Gly Val Ile Trp Gly Ser Glu Thr Thr Tyr Tyr Asn Ser Ala Leu Lys
        195                 200                 205

Ser Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Lys His Tyr Tyr Gly Gly Ser Tyr Ala Met Asp Tyr Trp Gly Gln
                245                 250                 255

Gly Thr Leu Val Thr Val Ser Ser
            260
```

<210> SEQ ID NO 25
<211> LENGTH: 264
<212> TYPE: PRT
<213> ORGANISM: Artificial Sequence
<220> FEATURE:
<223> OTHER INFORMATION: Synthetic Polypeptide

<400> SEQUENCE: 25

```
Met Glu Trp Thr Trp Val Phe Leu Phe Leu Leu Ser Val Thr Ala Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Arg Ala Ser Gln Asp Ile
        35                  40                  45
```

Ser Lys Tyr Leu Asn Trp Tyr Gln Gln Lys Pro Asp Gln Ala Pro Lys
    50                  55                  60

Leu Leu Ile Lys His Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Gly Asn Thr
            100                 105                 110

Leu Pro Tyr Thr Phe Gly Gln Gly Thr Lys Leu Glu Ile Lys Gly Ser
            115                 120                 125

Thr Ser Gly Ser Gly Lys Pro Gly Ser Gly Glu Gly Ser Thr Lys Gly
    130                 135                 140

Gln Val Gln Leu Gln Glu Ser Gly Pro Gly Leu Val Lys Pro Ser Gly
145                 150                 155                 160

Thr Leu Ser Leu Thr Cys Ala Val Ser Gly Val Ser Leu Pro Asp Tyr
                165                 170                 175

Gly Val Ser Trp Ile Arg Gln Pro Pro Gly Lys Gly Leu Glu Trp Ile
            180                 185                 190

Gly Val Ile Trp Gly Ser Glu Thr Thr Tyr Tyr Asn Ser Ala Leu Lys
            195                 200                 205

Ser Arg Val Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Leu Val Thr Val Ser Ser
            260

<210> SEQ ID NO 26
<211> LENGTH: 264
<212> TYPE: PRT
<213> ORGANISM: Artificial Sequence
<220> FEATURE:
<223> OTHER INFORMATION: Synthetic Polypeptide

<400> SEQUENCE: 26

Met Glu Trp Thr Trp Val Phe Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Lys Tyr Leu Asn Trp Tyr Gln Gln Lys Pro Gly Lys Ala Val Lys
    50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Lys Gly Ser
            115                 120                 125

Thr Ser Gly Ser Gly Lys Pro Gly Ser Gly Glu Gly Ser Thr Lys Gly
    130                 135                 140

Gln Val Gln Leu Gln Glu Ser Gly Pro Gly Leu Val Lys Pro Ser Glu
145                 150                 155                 160

Thr Leu Ser Val Thr Cys Thr Val Ser Gly Val Ser Leu Pro Asp Tyr
            165                 170                 175

Gly Val Ser Trp Ile Arg Gln Pro Pro Gly Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ser Lys Asp Thr Ser Lys Asn Gln Val Phe Leu
    210                 215                 220

Lys Met Ser Ser Leu Thr Ala Ala Asp Thr Ala Ile Tyr Tyr Cys Ala
225                 230                 235                 240

Lys His Tyr Tyr Tyr Gly Gly Ser Tyr Ala Met Asp Tyr Trp Gly Gln
            245                 250                 255

Gly Thr Leu Val Thr Val Ser Ser
            260

<210> SEQ ID NO 27
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 27

Arg Ala Ser Gln Asp Ile Ser Lys Tyr Leu Asn
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 28

His Thr Ser Arg Leu His Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 29

Gln Gln Gly Asn Thr Leu Pro Tyr Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 30

Gly Val Ser Leu Pro Asp Tyr
1               5

<210> SEQ ID NO 31

<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 31

Trp Gly Ser Glu Thr
1               5

<210> SEQ ID NO 32
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 32

His Tyr Tyr Tyr Gly Gly Ser Tyr Ala Met Asp Tyr
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

Asp Tyr Gly Val Ser
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 34

Val Ile Trp Gly Ser Glu Thr Thr Tyr Tyr Asn Ser Ala Leu Lys Ser
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 35

Gly Val Ser Leu Pro Asp Tyr Gly Val Ser
1               5                   10

<210> SEQ ID NO 36
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 36

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

```
Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
            100                 105

<210> SEQ ID NO 37
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 37

Glu Val Lys Leu Gln Glu Ser Gly Pro Gly Leu Val Ala Pro Ser Gln
 1               5                  10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
             35                  40                  45

Gly Val Ile Trp Gly Ser Glu Thr Thr Tyr Tyr Asn Ser Ala Leu Lys
 50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
             100                 105                 110

Gly Thr Ser Val Thr Val Ser Ser
 115                 120
```

HUMANIZED ANTIGEN-BINDING DOMAINS AND METHODS OF USE

CROSS REFERENCE TO RELATED APPLICATIONS

This application claims priority to U.S. Provisional Application 62/489,258 filed Apr. 24, 2017, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Apr. 24, 2017, is named K-1046_01SL_ST25.txt and is 43,305 bytes in size.

BACKGROUND OF THE INVENTION

Human cancers, by their very nature, comprise normal cells that have undergone a genetic or epigenetic conversion to become abnormal cancer cells. In doing so, cancer cells begin to express proteins and other antigens that are distinct from those expressed by normal cells and/or the proteins are expressed in significantly greater amounts than is expressed by normal cells.

Chimeric antigen receptors (CARs) and engineered T cell receptors (TCRs), which comprise binding domains capable of interacting with the cancer cell-expressed protein, allow T cells to target and kill cancer cells that express the particular protein. Similarly, antibodies that are conjugated to a therapeutic agent, are capable of selectively providing the therapeutic agent to cancer cells that express the particular protein and kill these cancer cells.

A need exists for CARs, TCRs, and antibodies comprising humanized antigen-binding domains for targeting and killing cancer cells.

SUMMARY OF THE INVENTION

The present invention addresses this need by providing compositions and methods including engineered immune cells that express chimeric antigen receptors (CARs) or T cell receptors (TCRs) having humanized antigen-binding domains; these CARs and TCRs specifically target and kill cancer cells. The present invention also addresses this need by providing compositions and methods including antibodies which specifically target and kill cancer cells.

An aspect of the present invention is humanized anti-CD19 antibody or antigen binding fragment thereof. The antibody comprises a light chain variable (VL) region and a heavy chain variable (VH) region, wherein the VL region comprises a VL complementarity determining region (CDR) 1 (VL CDR1), a VL CDR2, and a VL CDR3 and the VH region comprises a VH CDR1, a VL CDR2, and a VL CDR3. The VL region may be derived from SEQ ID NO: 36 and VH region is derived from SEQ ID NO: 37 and the VL and/or VH region comprise one or more amino acid substitutions in the framework region.

In some embodiments, the humanized anti-CD19 antibody or antigen binding fragment thereof of claim 1, wherein the VL region comprises up to 5, 10, 15, 20, 25, or 30 amino acids substitutions as compared to SEQ ID NO: 36.

In some embodiments, the one or more amino acids substitutions in the VL region are at positions corresponding to 7, 8, 10, 15, 22, 41, 42, 43, 44, 49, 71, 72, 77, 79, 80, 83, 87, 100, and/or 107 of SEQ ID NO: 36.

In some embodiments, the one or more amino acids substitutions in the VL region are selected from Ser at position 7, Pro at position 8, Val at position 15, Thr at position 22, Gln at position 41, Lys at position 42, Ala at position 43, Thr at position 72, Ser at position 77, Gln at position 79, Pro at position 80, and/or Lys at position 107 of SEQ ID NO: 36.

In some embodiments, the VH region comprises up to 5, 10, 15, 20, 25, 30, 35, 40, 45, or 50 amino acids substitutions as compared to SEQ ID NO: 37.

In some embodiments, the one or more amino acids substitutions in the VH region are at positions corresponding to 1, 3, 5, 9, 13, 15, 16, 17, 19, 20, 21, 23, 24, 37, 42, 48, 67, 69, 70, 71, 73, 76, 77, 78, 79, 81, 83, 86, 87, 88, 92, and/or 115 of SEQ ID NO: 37.

In some embodiments, the one or more amino acids substitutions in the VH region are at selected from Gln at position 1, Gln at position 3, Val at position 5, Gly at position 9, Lys at position 13, Gln at position 13, Gly at position 15, Arg at position 16, Thr at position 16, Thr at position 17, Arg at position 19, Leu at position 20, Ser at position 21, Ala at position 24, Gly at position 42, Ile at position 48, Phe at position 67, Ser at position 70, Arg at position 71, Thr at position 73, Asn at position 76, Thr at position 77, Leu at position 78, Tyr at position 79, Gln at position 81, Ser at position 83, Thr at position 86, Arg at position 86, Ala at position 87, Glu at position 88, Ala at position 88, Val at position 92, and/or Leu of SEQ ID NO: 37.

Another aspect of the present invention is a humanized anti-CD19 antibody or antigen binding fragment thereof comprising a light chain variable (VL) region and a heavy chain variable (VH) region. The VL region comprises a VL complementarity determining region (CDR) 1 (VL CDR1), a VL CDR2, and a VL CDR3 and the VH region comprises a VH CDR1, a VL CDR2, and a VL CDR3. The VL region has an amino acid sequence at least 85% identical to SEQ ID NO: 14, SEQ ID NO: 20, SEQ ID NO: 11, or SEQ ID NO: 17; and/or the VH region has an amino acid sequence at least 85% identical to SEQ ID NO: 15, SEQ ID NO: 21, SEQ ID NO: 12, or SEQ ID NO: 18.

In some embodiments, the antibody or the antigen binding fragment thereof is selected from the group consisting of an IgG, an Fab, an Fab', an F(ab')$_2$, an Fv, an scFv, and a single-domain antibody (dAB). In some embodiments, the antibody or antigen binding fragment thereof is an scFv.

In some embodiments, the VL CDR1 is at least 80% identical to SEQ ID NO: 27, the VL CDR2 is at least 80% identical to SEQ ID NO: 28, and the VL CDR3 is at least 80% identical to SEQ ID NO: 29.

In some embodiments, the VL CDR1 comprises SEQ ID NO: 27, the VL CDR2 comprises SEQ ID NO: 28, and the VL CDR3 comprises SEQ ID NO: 29.

In some embodiments, the VH CDR1 is at least 80% identical to SEQ ID NO: 30 or 33, the VH CDR2 is at least 80% identical to SEQ ID NO: 31 or 34, and the VH CDR3 is at least 80% identical to SEQ ID NO: 32.

In some embodiments, the VH CDR1 comprises SEQ ID NO: 30 or 33, the VH CDR2 comprises SEQ ID NO: 31 or 34, and the VH CDR3 comprises SEQ ID NO: 32.

In some embodiments, the VL CDR1 is at least 80% identical to SEQ ID NO: 27, the VL CDR2 is at least 80% identical to SEQ ID NO: 28, the VL CDR3 is at least 80% identical to SEQ ID NO: 29, the VH CDR1 is at least 80% identical to SEQ ID NO: 30 or 33, the VH CDR2 is at least 80% identical to SEQ ID NO: 31 or 34, and the VH CDR3 is at least 80% identical to SEQ ID NO: 32.

In some embodiments, the VL CDR1 comprises SEQ ID NO: 27, the VL CDR2 comprises SEQ ID NO: 28, the VL CDR3 comprises SEQ ID NO: 29, the VH CDR1 comprises SEQ ID NO: 30 or 33, the VH CDR2 comprises SEQ ID NO: 31 or 34, and the VH CDR3 comprises SEQ ID NO: 32.

In some embodiments, the VL CDR1 comprises SEQ ID NO: 27, the VL CDR2 comprises SEQ ID NO: 28, the VL CDR3 comprises SEQ ID NO: 29, the VH CDR1 comprises SEQ ID NO: 30, the VH CDR2 comprises SEQ ID NO: 31, and the VH CDR3 comprises SEQ ID NO: 32.

In some embodiments, the VL CDR1 comprises SEQ ID NO: 27, the VL CDR2 comprises SEQ ID NO: 28, the VL CDR3 comprises SEQ ID NO: 29, the VH CDR1 comprises SEQ ID NO: 33, the VH CDR2 comprises SEQ ID NO: 34, and the VH CDR3 comprises SEQ ID NO: 32.

In some embodiments, the VL CDR1 comprises SEQ ID NO: 27, the VL CDR2 comprises SEQ ID NO: 28, the VL CDR3 comprises SEQ ID NO: 29, the VH CDR1 comprises SEQ ID NO: 30, the VH CDR2 comprises SEQ ID NO: 34, and the VH CDR3 comprises SEQ ID NO: 32.

In some embodiments, the VL is at least 85% identical to SEQ ID NO: 14.

In some embodiments, the VH is at least 85% identical to SEQ ID NO: 15.

In some embodiments, the VL is at least 85% identical to SEQ ID NO: 14 and the VH is at least 85% identical to SEQ ID NO: 15. In some embodiments, the VL is at least 90% identical to SEQ ID NO: 14 and the VH is at least 90% identical to SEQ ID NO: 15. In some embodiments, the VL is at least 95% identical to SEQ ID NO: 14 and the VH is at least 95% identical to SEQ ID NO: 15. In some embodiments, the VL is at least 99% identical to SEQ ID NO: 14 and the VH is at least 99% identical to SEQ ID NO: 15. In some embodiments, the VL comprises SEQ ID NO: 14 and the VH comprises SEQ ID NO: 15.

In some embodiments, the polypeptide comprises SEQ ID NO: 24.

In some embodiments, the VL is at least 85% identical to SEQ ID NO: 20.

In some embodiments, the VH is at least 85% identical to SEQ ID NO: 21.

In some embodiments, the VL is at least 85% identical to SEQ ID NO: 20 and the VH is at least 85% identical to SEQ ID NO: 21. In some embodiments, the VL is at least 90% identical to SEQ ID NO: 20 and the VH is at least 90% identical to SEQ ID NO: 21. In some embodiments, the VL is at least 95% identical to SEQ ID NO: 20 and the VH is at least 95% identical to SEQ ID NO: 21. In some embodiments, the VL is at least 99% identical to SEQ ID NO: 20 and the VH is at least 99% identical to SEQ ID NO: 21. In some embodiments, the VL comprises SEQ ID NO: 20 and the VH comprises SEQ ID NO: 21.

In some embodiments, the polypeptide comprises SEQ ID NO: 26.

In some embodiments, the VL is at least 85% identical to SEQ ID NO: 11.

In some embodiments, the VH is at least 85% identical to SEQ ID NO: 12.

In some embodiments, the VL is at least 85% identical to SEQ ID NO: 11 and the VH is at least 85% identical to SEQ ID NO: 12. In some embodiments, the VL is at least 90% identical to SEQ ID NO: 11 and the VH is at least 90% identical to SEQ ID NO: 12. In some embodiments, the VL is at least 95% identical to SEQ ID NO: 11 and the VH is at least 95% identical to SEQ ID NO: 12. In some embodiments, the VL is at least 99% identical to SEQ ID NO: 11 and the VH is at least 99% identical to SEQ ID NO: 12. In some embodiments, the VL comprises SEQ ID NO: 11 and the VH comprises SEQ ID NO: 12.

In some embodiments, the polypeptide comprises SEQ ID NO: 23.

In some embodiments, the VL is at least 85% identical to SEQ ID NO: 17.

In some embodiments, the VH is at least 85% identical to SEQ ID NO: 18.

In some embodiments, the VL is at least 85% identical to SEQ ID NO: 17 and the VH is at least 85% identical to SEQ ID NO: 18. In some embodiments, the VL is at least 90% identical to SEQ ID NO: 17 and the VH is at least 90% identical to SEQ ID NO: 18. In some embodiments, the VL is at least 95% identical to SEQ ID NO: 17 and the VH is at least 95% identical to SEQ ID NO: 18. In some embodiments, the VL is at least 99% identical to SEQ ID NO: 17 and the VH is at least 99% identical to SEQ ID NO: 18. In some embodiments, the VL comprises SEQ ID NO: 17 and the VH comprises SEQ ID NO: 18.

In some embodiments, the polypeptide comprises SEQ ID NO: 25.

Another aspect of the present invention is a polypeptide encoded by the humanized anti-CD19 antibody of an above aspect or embodiment.

In some embodiments, the polypeptide comprises a His Tag comprising an amino acid sequence of SEQ ID NO: 8.

In some embodiments, the polypeptide is at least 85% identical to SEQ ID NO: 10, SEQ ID NO: 13, SEQ ID NO: 16, or SEQ ID NO: 19. In some embodiments, the polypeptide is at least 90% identical to SEQ ID NO: 10, SEQ ID NO: 13, SEQ ID NO: 16, or SEQ ID NO: 19. In some embodiments, the polypeptide is at least 95% identical to SEQ ID NO: 10, SEQ ID NO: 13, SEQ ID NO: 16, or SEQ ID NO: 19. In some embodiments, the polypeptide is at least 99% identical to SEQ ID NO: 10, SEQ ID NO: 13, SEQ ID NO: 16, or SEQ ID NO: 19. In some embodiments, the polypeptide comprises SEQ ID NO: 10, SEQ ID NO: 13, SEQ ID NO: 16, or SEQ ID NO: 19.

In some embodiments, the polypeptide is linked to a therapeutic agent. In some embodiments, the therapeutic agent is a chemotherapeutic agent, a cytokine, a radioactive atom, an siRNA, or a toxin. In some embodiments, the therapeutic agent is a chemotherapeutic agent.

In some embodiments, the agent is a radioactive atom.

Yet another aspect of the present invention is a chimeric antigen receptor (CAR) or a T cell receptor (TCR). The CAR or TCR comprises (i) an antigen binding domain, (ii) a costimulatory domain, and (iii) an activating domain. The costimulatory domain comprises an extracellular domain, a transmembrane domain, and an intracellular domain, and the antigen binding domain comprises at least the polypeptide of claim 52.

In some embodiments, the costimulatory domain is from or is derived from CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103

(ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof.

In some embodiments, the transmembrane domain is from or is derived from 4-1BB/CD137, an alpha chain of a T cell receptor, a beta chain of a T cell receptor, CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and combinations thereof.

In some embodiments, the intracellular domain is from or is derived from 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, or VLA-6, or a combination thereof.

In some embodiments, the extracellular domain is from or is derived from CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof.

In some embodiments, the activating domain is from or is derived from CD3-zeta or CD3-episilon.

An aspect of the present invention is a humanized anti-CD19 antibody or antigen binding fragment thereof encoding the CAR or TCR of an above aspect or embodiment.

Yet another aspect of the present invention is a vector comprising the humanized anti-CD19 antibody or antigen binding fragment of an above aspect or embodiment.

In some embodiments, the vector is an adenoviral vector, an adenovirus-associated vector, a DNA vector, a lentiviral vector, a plasmid, a retroviral vector, or an RNA vector. In some embodiments, the vector is a retroviral vector. In some embodiments, the retroviral vector is a lentiviral vector.

Another aspect of the present invention is chimeric antigen receptor (CAR) or T Cell Receptor (TCR) encoded by the vector of an above aspect or embodiment.

Yet another aspect of the present invention is a cell comprising a humanized anti-CD19 antibody or antigen binding fragment thereof of an above aspect or embodiment, a vector of an above aspect or embodiment, or a chimeric antigen receptor (CAR) or T cell receptor (TCR) of an above aspect or embodiment.

In some embodiments, the cell is a T cell.

In some embodiments, the T cell is an allogeneic T cell, an autologous T cell, an engineered autologous T cell (eACT), or a tumor-infiltrating lymphocyte (TIL).

In some embodiments, the T cell is a CD4+ T cell.

In some embodiments, the T cell is a CD8+ T cell.

In some embodiments, the cell is an in vitro cell.

In some embodiments, the T cell is an autologous T cell.

In some embodiments, the cell produces at least Interferon gamma (IFNγ) upon binding to human CD19.

An aspect of the present invention is a composition comprising a plurality of cells of an above aspect or embodiment.

In some embodiments, the composition comprises CD4+ or CD8+ cells. In some embodiments, the composition comprises CD4+ and CD8+ cells. In some embodiments, between about 20% and 80% of the T cells are CD4+ cells and the rest of the T cells are CD8+ cells. In some embodiments, between about 30% and 70% of the T cells are CD4+ cells and the rest of the T cells are CD8+ cells. In some embodiments, between about 40% and 60% of the T cells are CD4+ cells and the rest of the T cells are CD8+ cells. In some embodiments, about 50% of the T cells are CD4+ cells and about 50% of the T cells are CD8+ cells.

In some embodiments, each cell in the plurality of cells is an autologous T cell.

In some embodiments, the composition comprises at least one pharmaceutically-acceptable excipient.

Another aspect of the present invention is a composition comprising a humanized anti-CD19 antibody or antigen binding fragment thereof of an above aspect or embodiment, a vector of an above aspect or embodiment, or a chimeric antigen receptor (CAR) or T cell receptor (TCR) of an above aspect or embodiment.

Yet another aspect of the present invention is a method for manufacturing a cell expressing a chimeric antigen receptor (CAR) or a T cell receptor (TCR). The method comprises a step of transducing a cell with a humanized anti-CD19 antibody or antigen binding fragment thereof of an above aspect or embodiment or a vector of an above aspect or embodiment.

In some embodiments, the cell is a lymphocyte isolated from a patient in need of treatment.

In some embodiments, the lymphocyte is a natural killer cell, a T cell, or a B cell.

In some embodiments, the method further comprises a step of culturing the cell under conditions that promote cellular proliferation and/or T cell activation.

In some embodiments, the method further comprises a step of isolating desired T cells.

In some embodiments, the step of isolating desired T cells occurs after about six days of culturing.

In some embodiments, the desired T cells express CD4+ and/or CD8+.

Yet another aspect of the present invention is a method for treating a B-cell lymphoma comprising administering to a subject in need thereof a cell of an above aspect or embodiment or a composition of an above aspect or embodiment.

In some embodiments, the B-cell lymphoma is selected from the group consisting of Acute Lymphoblastic Leukemia (ALL), AIDS-related lymphoma, ALK-positive large B-cell lymphoma, Burkitt's lymphoma, Chronic lymphocytic leukemia, CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia. In some embodiments, the B-cell lymphoma is selected from the group consisting of Acute Lymphoblastic Leukemia (ALL), Chronic lymphocytic leukemia, CLL), Diffuse large B-cell lymphoma (DLBCL), Follicular lymphoma, Mantle cell lymphoma (MCL), Marginal zone B-cell lymphoma (MZL), Mucosa-Associated Lymphatic Tissue lymphoma (MALT), and Non-Hodgkin's lymphoma. In some embodiments, the B-cell lymphoma is Non-Hodgkin's lymphoma.

Generally, the present invention relates to Engineered Autologous Cell Therapy, abbreviated as "eACT™," also known as adoptive cell transfer eACT™, is a process by which a patient's own T cells are collected and subsequently genetically engineered to recognize and target one or more antigens expressed on the cell surface of one or more specific cancer indications. T cells may be engineered to express, for example, a chimeric antigen receptor (CAR) or T Cell Receptor (TCR). See, FIG. 1A, FIG. 1B, and FIG. 2. CAR positive (CAR+) T cells are engineered to express a CAR. CARs may comprise, e.g., a humanized single chain variable fragment (scFv) with specificity for a particular tumor antigen, e.g., human CD19. The scFV may be directly or indirectly linked to an intracellular signaling part comprising at least one costimulatory domain, which, in turn, is directly or indirectly linked to at least one activating domain. The components of a CAR may be arranged in any order. Examples of CAR T cell therapies and constructs are described in U.S. Patent Publication Nos. 2013/0287748, 2014/0227237, 2014/0099309, and 2014/0050708; U.S. Provisional Application Nos. 62/470,703 and 62/317,258; International Patent Publications Nos. WO2012033885, WO2012079000, WO2014127261, WO2014186469, WO2015080981, WO2015142675, WO2016044745, and WO2016090369; and Rosenberg and Restifo, *Cancer Immunology and Immunotherapy*, 348: 62-68 (2015), each of which is incorporated by reference in its entirety.

Additionally, the present invention generally relates to a humanized single chain variable fragment (scFv) with specificity for human CD19. The humanized scFV anti-human CD19 scFV can be conjugated (e.g., linked to) to a therapeutic agent (e.g., a chemotherapeutic agent and a radioactive atom) for binding to a cancer cell, delivering the therapeutic agent to the cancer cell, and killing the cancer cell which expresses human CD19.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference.

Other features and advantages of the invention will be apparent from the Drawings and the following Detailed Description, including the Examples, and the claims.

BRIEF DESCRIPTION OF THE FIGURES

The above and further features will be more clearly appreciated from the following detailed description when taken in conjunction with the accompanying drawings. The drawings however are for illustration purposes only; not for limitation.

FIG. 1A shows an exemplary polynucleotide encoding a CAR, a viral vector comprising the CAR-encoding polynucleotide, transduction of the viral vector into a patient's T cell, integration into the host genome, and expression of a CAR on the surface of the transduced ("CAR-engineered") T cell FIG. 1B shows a CAR-engineered T cell which has recognized a target antigen located on the surface of a cancer cell. Recognition and binding of the target antigen activates mechanisms in the T cell including cytolytic activity, cytokine release, and T cell proliferation; these mechanisms promote killing of the cancer cells.

In FIG. 5A, thermostability was determined in the presence of 50 mM NaCl and in FIG. 5B, NaCl was omitted. The CAR derived from scFvs AS ("□"), SS ("Δ"), JS ("◊"), and NS ("X") are shown.

FIG. 7A), Namalawa (CD19+*Homo sapiens* Burkitt's lymphoma cells; FIG. 7B), Eol-1 (CD19− *Homo sapiens* acute myeloid (eosinophilic) leukemia cells; FIG. 7C), and Mv411 (CD19− *Homo sapiens* biphenotypic B myelomonocytic leukemia cells; FIG. 7D). Staurosporine ("Stauro") was used as a positive control for tumor cell killing.

DETAILED DESCRIPTION OF THE INVENTION

Figure 1A:
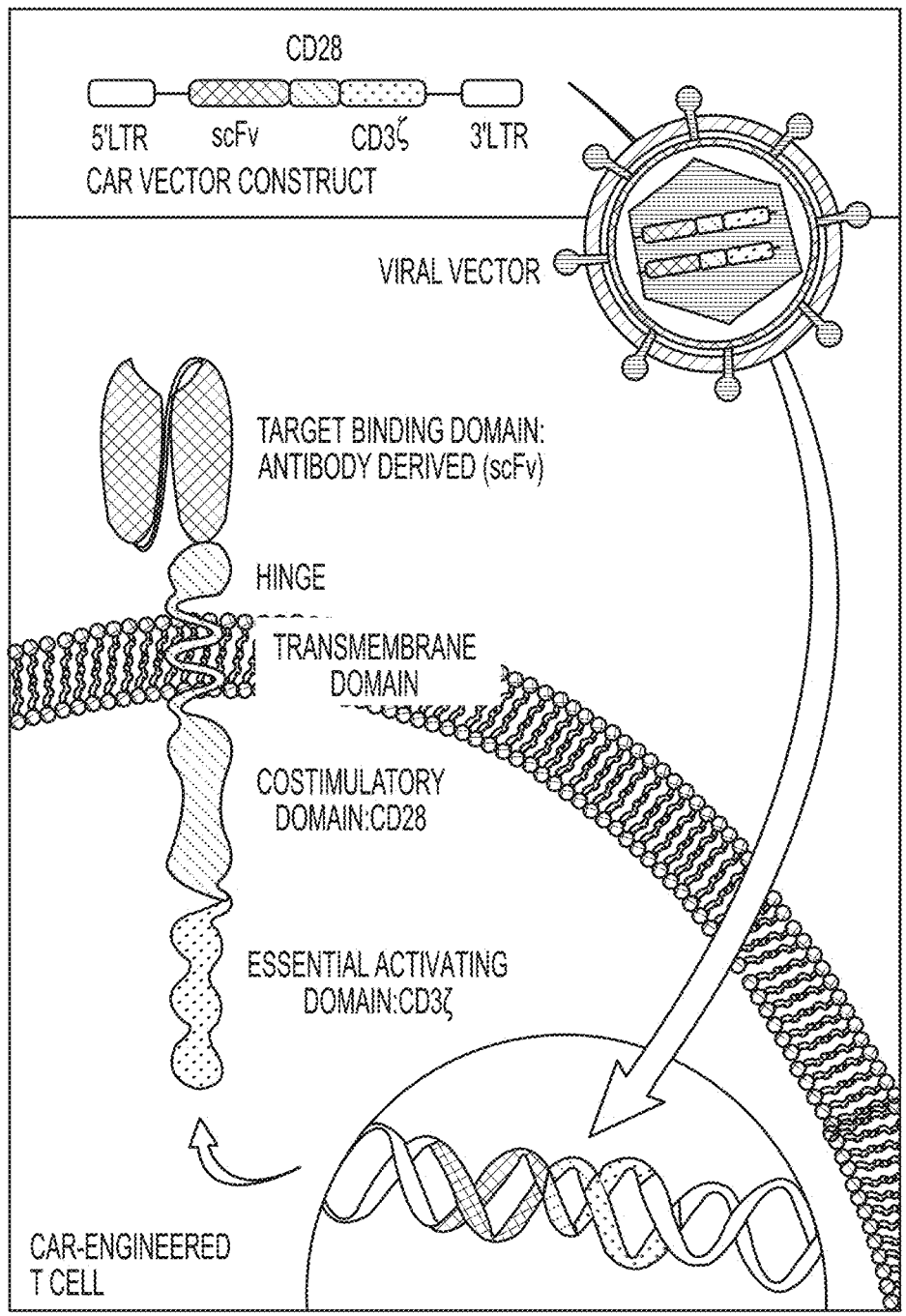
FIG. 1A and FIG. 1B are cartoons depicting features of chimeric antigen receptor (CAR) manufacture and use.

The present invention relates to novel polypeptides comprising humanized antigen binding domains which recognize and bind human CD19 and polynucleotides encoding the same. Some aspects of the invention relate to a polynucleotide encoding a chimeric antigen receptor (CAR) or a T cell receptor (TCR) comprising the humanized anti-human CD19 antigen binding domain. The present invention also provides vectors (e.g., viral vectors) comprising such polynucleotides and compositions comprising such vectors. The present invention further provides polynucleotides encoding such CARs or TCRs and compositions comprising such polynucleotides. The present invention additionally provides engineered cells (e.g., T cells) comprising such polynucleotides and/or transduced with such viral vectors and compositions comprising such engineered cells. The present invention provides compositions (e.g., pharmaceutical compositions) including a plurality of engineered T cells. The present invention provides methods for manufacturing such engineered T cells and compositions and uses (e.g., in treating a B cell lymphoma) of such engineered T cells and compositions. And, the present invention provides a method of inducing an immunity against a tumor comprising administering to a subject an effective amount of a cell comprising a polynucleotide, a vector, or a polypeptide of the present invention. Other aspects of the invention relate to cells comprising the CAR or the TCR and their use in a T cell therapy, e.g., an autologous cell therapy (eACT™), for the treatment of a patient suffering from a cancer.

Definitions

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include, but not limited to, at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided. Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", $2^{nd}$ ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, an antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In certain embodiments, antibodies described herein refer to polyclonal antibody populations.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "amino acid sequence derived from an antibody" may be physically derived, e.g., expressed from a fragment of a polynucleotide encoding the antibody, or may be in silico derived, e.g., the nucleotide sequence determined to encode the antibody (or fragment thereof) is used to synthesize an artificial polynucleotide sequence (or fragment) and the artificial polynucleotide sequence is expressed as the antibody, or fragment thereof.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to CD19. In further embodiments, the antigen binding molecule is an antibody fragment that specifically binds to the antigen, including one or more of the complementarity determining regions (CDRs) thereof.

In further embodiments, the antigen binding molecule is a single chain variable fragment (scFv). A scFv polypeptide molecule is a covalently linked $V_H$::$V_L$ heterodimer, which can be expressed from a gene fusion including $V_H$- and $V_L$-encoding genes linked by a peptide-encoding linker. (See Huston et al. (1988) *Proc Nat Acad Sci USA* 85(16): 5879-5883). The linker peptide (e.g., of about ten to about 25 amino acids) is usually rich in glycine for flexibility, as well as serine or threonine for solubility. The linker may either connect the N-terminus of the VH with the C-terminus of the VL or connect the C-terminus of the VH with the N-terminus of the VL. This protein retains the specificity of the original immunoglobulin, despite removal of the constant regions and the introduction of the linker. An scFv may also include an N-terminal peptide sequence, which sometimes is referred to as a "signal peptide" or "leader sequence". A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies (See Barbas et al., Proc. Natl. Acad. Sci. USA 89:9339-43 (1992); Zebedee et al., Proc. Natl. Acad. Sci. USA 89:3175-79 (1992)).

As used herein, the term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL", "VL region", and "VL domain" are used interchangeably to refer to the light chain variable region of an antigen binding domain such as an antibody or an antigen-binding fragment thereof, and comprise one, two, or all three CDRs.

The terms "VH", "VH region", and "VH domain" are used interchangeably to refer to the heavy chain variable region of an antigen binding domain such as an antibody or an antigen-binding fragment thereof, and comprise one, two, or all three CDRs.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

TABLE 2

CDRs for the light chain variable (VL) region of the FMC63 anti-CD19 antibody or a fragment thereof

| Sequence (Convention) | CDR1 | SEQ ID NO | CDR2 | SEQ ID NO | CDR3 | SEQ ID NO |
|---|---|---|---|---|---|---|
| VL (Chothia) | RASQDISKYLN | 27 | HTSRLHS | 28 | QQGNTLPYT | 29 |
| VL (Kabat) | RASQDISKYLN | 27 | HTSRLHS | 28 | QQGNTLPYT | 29 |
| VL (IMGT) | RASQDISKYLN | 27 | HTSRLHS | 28 | QQGNTLPYT | 29 |

TABLE 3

CDRs for the heavy chain variable (VH) region of the FMC63 anti-CD19 antibody or fragment thereof

| Sequence (Convention) | CDR1 | SEQ ID NO | CDR2 | SEQ ID NO | CDR3 | SEQ ID NO |
|---|---|---|---|---|---|---|
| VH (Chothia) | GVSLPDY | 30 | WGSET | 31 | HYYYGGSYAMDY | 32 |
| VH (Kabat) | DYGVS | 33 | VIWGSETTYYNSALKS | 34 | HYYYGGSYAMDY | 32 |
| VH (IMGT) | GVSLPDYGVS | 30 | VIWGSETTYYNSALKS | 34 | HYYYGGSYAMDY | 32 |

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIA-CORE® or KinExA.

CD19 (also known as Cluster of Differentiation 19, B-lymphocyte antigen CD19, B-lymphocyte surface antigen B4, B4, CVID3, Differentiation antigen CD19) is a protein that in humans is encoded by the CD19 gene. It is found on the surface of B cells. Since CD19 is a hallmark of B cells, it may be a useful antigen for recognizing and cancer cells that arise from this type of B cells, i.e., B-cell lymphomas.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain.

As, used herein, the term "heterologous" means from any source other than naturally occurring sequences. For example, a heterologous sequence, included as a part of a costimulatory protein having the amino acid sequence of SEQ ID NO: 1, e.g., the corresponding human costimulatory protein, is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software known in the art, e.g., Refmac and Phenix. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In a specific embodiment, provided herein is an antibody or an antigen binding molecule thereof that binds to a target human antigen, e.g., human CD19, with higher affinity than to another species of the target antigen, e.g., a non-human CD19. In certain embodiments, provided herein is an antibody or an antigen binding molecule t thereof that binds to the target human antigen, e.g., human CD19, with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of human CD19.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "autologous" mean any material derived from the same individual to which it is later to be re-introduced. For example, the Engineered Autologous Cell Therapy (eACT™), also known as adoptive cell transfer, is a process by which a patient's own T cells are collected and subsequently genetically engineered to express a polynucleotide, e.g., a polynucleotide encoding a CAR that recognizes and targets one or more antigens expressed on the cell surface of one or more specific tumor cells or malignancies, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

As used herein, the terms "genetic engineering" or "engineering" are used interchangeably and mean a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR), which is incorporated into the cell's genome.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, myeloma, and other leukocyte malignancies.

Cancers that may be treated include B-cell lymphomas, Acute Lymphoblastic Leukemia (ALL), AIDS-related lymphoma, ALK-positive large B-cell lymphoma, Burkitt's lymphoma, Chronic lymphocytic leukemia, CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia, or a combination thereof. In one embodiment, the B-cell lymphoma is Acute Lymphoblastic Leukemia (ALL), Chronic lymphocytic leukemia, CLL), Diffuse large B-cell lymphoma (DLBCL), Follicular lymphoma, Mantle cell lymphoma (MCL), Marginal zone B-cell lymphoma (MZL), Mucosa-Associated Lymphatic Tissue lymphoma (MALT), and Non-Hodgkin's lymphoma. In one embodiment, the B-cell lymphoma is Non-Hodgkin's lymphoma.

The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six known types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B cells, on the other hand, play a principal role in humoral immunity (with antibody involvement). B cells make antibodies, process antigens to perform the role of antigen-presenting cells (APCs), and develop into memory B cells after activation by antigen interaction. In mammals, immature B cells develop in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CARs) or T cell receptors (TCRs) or both. CAR positive (+) T cells are engineered to express one or more extracellular single chain variable fragments (scFvs) with specificity for a particular tumor antigen linked to an intracellular signaling part comprising at least one costimulatory domain and at least one activating domain. The costimulatory domain can be derived from a naturally-occurring costimulatory domain or a variant thereof, and the activating domain can be derived from, e.g., CD3-zeta and CD3-episilon. In certain embodiments, the CAR is designed to have two, three, four, or more costimulatory domains. The CAR scFv can be designed to target, for example, human CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708 and U.S. Provisional Application Nos. 62/470,703 and 62/317,258; these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell can include a T cell.

The terms "peptide," "polypeptide," and "protein" are used interchangeably, and refer to a compound comprising amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell (APC) that specifically binds a cognate co-stimulatory molecule on a T cell. Alternately/additionally, an antibody (e.g., an anti-CD28 antibody) can be a costimulatory ligand when bound to a plate, a bead, an APC, or in solution. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A costimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1 A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Various aspects of the invention are described in further detail in the following subsections.

I. Chimeric Antigen Receptors and T Cell Receptors

Chimeric antigen receptors (CARs or CAR-Ts) and T cell receptors (TCRs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

Figure 1B:
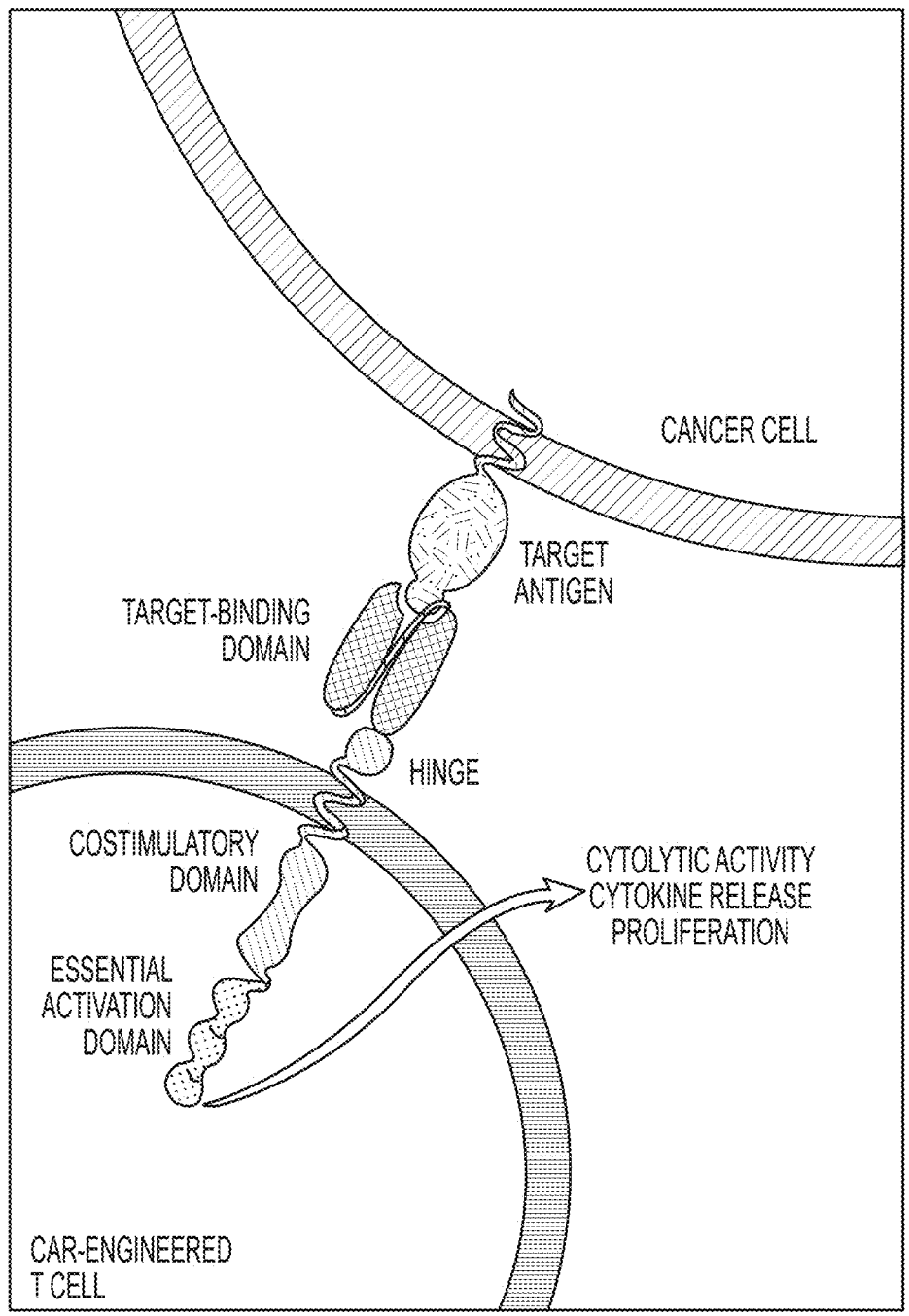
Figure 2:
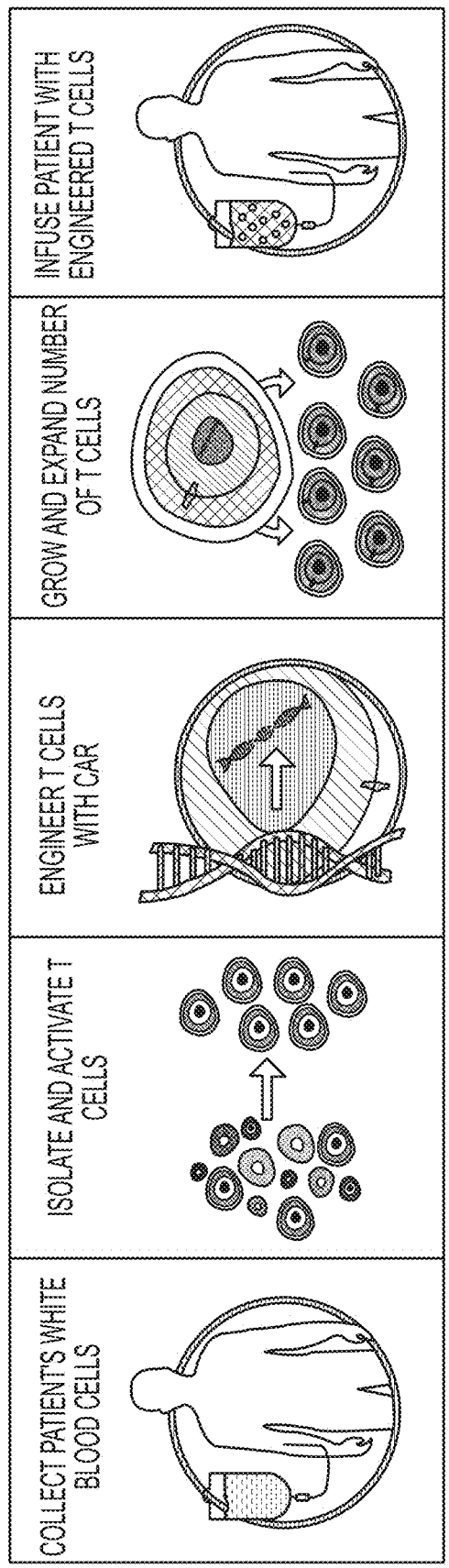
FIG. 2 is a cartoon showing major steps performed during Engineered Autologous Cell Therapy (eACT™).

Steps performed in manufacturing a cell that expresses a CAR are shown in FIG. 1A and the mechanism of CAR-mediated killing mediated via recognition of target on a tumor cell is shown in FIG. 1B.

The present invention relates to chimeric antigen receptors (CARs) and T cell receptors (TCR) comprising an antigen binding domain, such as an scFv, that specifically binds to human CD19 and engineered T cells comprising an antigen binding domain that specifically binds to human CD19. In some embodiments, an antigen binding domain of the present invention is an scFv derived from an antibody, e.g., FMC63 antibody Other antibodies directed to human CD19 may be used.

An anti-human CD19 CAR or TCR of the present invention comprises an antigen binding domain that specifically binds to human CD19. In some embodiments, the anti-human CD19 CAR or TCR further comprises a costimulatory domain, and/or an extracellular domain (i.e., a "hinge" or "spacer" region), and/or a transmembrane domain, and/or an intracellular (signaling) domain, and/or a CD3-zeta or CD3-epsilon activation domain. In some embodiments, the anti-human CD19 CAR or TCR comprises an scFv antigen binding domain that specifically binds human CD19, a costimulatory domain, an extracellular domain, a transmembrane domain, and a CD3-zeta or CD3-epsilon activating domain.

In some embodiments, an orientation of the CARs in accordance with the invention comprises an antigen binding domain (such as an scFv) in tandem with a costimulatory domain and an activating domain. The costimulatory domain can comprise one or more of an extracellular portion, a transmembrane portion, and an intracellular portion. In other embodiments, multiple costimulatory domains can be utilized in tandem.

I.A. Antigen Binding Domains

CARs can be engineered to bind to an antigen (such as a cell-surface antigen) by incorporating an antigen binding molecule that interacts with a specific targeted antigen. In some embodiments, the antigen binding molecule is an antibody fragment thereof, e.g., one or more single chain antibody fragments ("scFv"). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they can be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

The present invention relates to anti-human CD19 antibodies, fragments thereof, e.g., scFvs, chimeric antigen receptors (CARs), and T cell receptor (TCRs) having humanized antigen binding domains.

The below nucleotide sequences are shown in the format of "Leader sequence-VL-Linker-VH-His Tag-stop codon", i.e., the "Leader sequence" is in bold font, the "Linker" is in italics, the "His Tag" is in bold italics, and the VL, VH, and "stop codon" are in standard font.

WT-FMC63-scFv (SEQ ID NO: 1)
ATGGAATGGACCTGGGTGTTCCTGTTCCTGCTGAGCGTGACAGCCGGCGT

GCACTCTGACATCCAAATGACGCAAACGACCTCAAGTCTGTCCGCGAGCC

TGGGCGACCGTGTTACGATTAGCTGCCGTGCTTCACAAGATATCAGTAAA

TACCTGAACTGGTATCAGCAAAAACCGGATGGTACCGTTAAACTGCTGAT

CTATCATACGTCTCGTCTGCACAGTGGCGTCCCGTCCCGCTTTAGCGGTT

CTGGCAGTGGTACCGATTATTCACTGACGATTTCGAACCTGGAACAGGAA

GACATCGCGACCTACTTTTGCCAGCAAGGTAATACCCTGCCGTATACGTT

CGGCGGTGGCACCAAACTGGAAATCACC*GGCTCCACGTCAGGCTCGGGTA*

*AACCGGGCAGCGGTGAAGGCTCTACCAAAGGTGAAGTCAAACTGCAGGAA*

AGCGGTCCGGGTCTGGTCGCACCGAGCCAATCTCTGAGTGTGACCTGTAC

GGTGTCGGGTGTTAGCCTGCCGGATTACGGCGTGTCATGGATTCGTCAGC

CGCCGCGTAAAGGTCTGGAATGGCTGGGTGTTATCTGGGGCTCGGAAACC

ACGTATTACAATAGTGCACTGAAATCCCGTCTGACCATTATCAAAGACAA

CTCCAAATCACAGGTTTTCCTGAAAATGAACAGCCTGCAAACCGATGACA

CGGCGATCTATTACTGCGCGCAAACATTATTACTATGGTGGCTCTTATGCT

ATGGATTATTGGGGTCAAGGCACCTCGGTTACGGTCTCGTCATGAT

*CATCATCATCATCATCAT*AA.

SS-scFv (SEQ ID NO: 2)
ATGGAATGGACCTGGGTGTTCCTGTTCCTGCTGAGCGTGACAGCCGGCGT

GCACTCTGACATCCAAATGACCCAGTCGCCGTCCTTTCTGAGCGCAAGCG

TCGGTGACCGTGTTACGATTACCTGCCGTGCCAGCCAAGACATCTCTAAA

TACCTGAACTGGTATCAGCAAAAACCGGATCAGGCACCGAAACTGCTGAT

CAAACATACCTCACGTCTGCACTCGGGTGTCCCGAGCCGCTTTAGTGGTT

CCGGCTCAGGTACCGATTTTACCTTCACGATTAGCTCTCTGCAGCCGGAA

GACATCGCCACGTATTACTGCCAGCAAGGTAATACCCTGCCGTACACGTT

CGGCCAAGGTACCAAACTGGAAATCAAA*GGCTCGACGAGCGGCTCTGGTA*

*AACCGGGCTCTGGTGAAGGCAGTACCAAAGGTGAAGTGCAGCTGGTTGAA*

AGCGGTGGTGGTCTGGTTCAACCGGGTCGTTCCCTGCGTCTGTCATGTAC

GGCGAGTGGTGTCTCCCTGCCGGACTATGGCGTCTCCTGGGTGCGTCAGC

CGCCGGGTAAAGGTCTGGAATGGATTGGTGTGATCTGGGGCAGTGAAACC

ACGTATTACAACTCGGCCCTGAAAAGCCGTTTTACCATTTCTCGCGATAA

CAGTAAAAATACGCTGTACCTGCAGATGAATAGCCTGCGCGCGGAAGACA

CCGCCGTTTACTACTGCGCAAAACATTACTACTACGGTGGCAGCTATGCT

ATGGACTACTGGGGTCAGGGCACGCTGGTTACGGTGTCGTCATGAT

*CATCATCATCATCATCAT*AA.

JS-scFv (SEQ ID NO: 3)
ATGGAATGGACCTGGGTGTTCCTGTTCCTGCTGAGCGTGACAGCCGGCGT

GCACTCTGATATTCAAATGACCCAGTCCCCGTCCTCCCTGAGTGCCTCCG

TCGGTGACCGTGTTACGATTACCTGCCGTGCGAGCCAAGACATCTCTAAA

TACCTGAACTGGTATCAGCAAAAACCGGATCAGGCACCGAAACTGCTGAT

CAAACATACCTCACGTCTGCACTCGGGTGTGCCGAGCCGCTTTAGTGGTT

CCGGCTCAGGTACCGATTACACCCTGACGATCAGCTCTCTGCAGCCGGAA

GACTTTGCCACGTATTACTGCCAGCAAGGTAATACCCTGCCGTATACGTT

CGGCCAAGGTACCAAACTGGAAATCAAA*GGCTCGACGAGCGGCTCTGGTA*

*AACCGGGCTCTGGTGAAGGCAGTACCAAAGGTGAAGTGCAGCTGGTTGAA*

AGCGGTGGTGGTCTGGTTCAACCGGGTCGTTCCCTGCGTCTGTCATGTAC

GGCGAGTGGTGTCTCCCTGCCGGACTATGGCGTGTCCTGGATTCGTCAGC

CGCCGGGTAAAGGCCTGGAATGGATTGGTGTCATCTGGGGCAGTGAAACC

ACGTATTACAACTCGGCCCTGAAAAGCCGTTTCACCATCTCTCGCGATAA

CAGTAAAAATACGCTGTACCTGCAGATGAATAGCCTGCGCGCGGAAGACA

CCGCCGTTTACTACTGCGCAAAACATTACTACTACGGTGGCAGCTATGCT

ATGGATTACTGGGGTCAAGGCACGCTGGTCACCGTTTCGTCATGAT

*CATCATCATCATCATCAC*AA.

AS-scFv (SEQ ID NO: 4)
ATGGAATGGACCTGGGTGTTCCTGTTCCTGCTGAGCGTGACAGCCGGCGT

GCACTCTGACATTCAGATGACGCAAAGTCCGAGTCCGGTTCAGGCACCGA

-continued

TTTTACCTTCACGATTAGCTCTCTGCAACCGGAAGACATCGCCACGTATT

ACTGCCAGCAAGGCAATACCCTGCCGTACACGTTCGGTCAGGGCACCAAA

CTGGAAATCAAA*GGTTCGACGAGCGGTTCTGGCAAACCGGGTTCTGGCGA*

*AGGTAGTACCAAAGGC*CAGGTCCAACTGCAGGAAAGCGGCCCGGGTCTGG

TGAAACCGTCCGGTACCCTGTCACTGACGTGTGCGGTGAGTGGCGTTTCC

CTGCCGGACTATGGTGTTTCCTGGATTCGTCAACCGCCGGGCAAAGGTCT

GGAATGGATTGGCGTCATCTGGGGTAGTGAAACCACGTATTACAACTCGG

CCCTGAAAAGCCGTGTGACCATCTCTCGCGATAACAGTAAAAATACGCTG

TACCTGCAGATGAATAGCCTGCGCGCGGAAGACACCGCCGTTTACTACTG

CGCAAAACATTACTACTACGGCGGTAGCTATGCTATGGATTACTGGGGTC

AAGGCACGCTGGTTACGGTTTCCTCG*CATCATCATCATCATCAC*TGATA

A.

NS-scFv (SEQ ID NO: 5)

ATGGAATGGACCTGGGTGTTCCTGTTCCTGCTGAGCGTGACAGCCGGCGT

GCACTCTGACATTCAGATGACACAGAGCCCTTCTTCCCTGAGCGCCAGCG

TCGGAGATAGAGTGACCATTACTTGTAGAGCCAGCCAGGACATTTCCAAA

TACCTGAACTGGTATCAGCAGAAGCCCGGGAAAGCTGTGAAGCTGCTGAT

CTACCACACCTCTCGGCTGCATAGTGGAGTCCCTTCAAGATTCTCAGGCA

GCGGGTCCGGAACTGACTATACTCTGACCATCAGCTCCCTGCAGCCTGAG

GATATTGCAACCTACTTCTGCCAGCAGGGCAATACCCTGCCATATACATT

TGGCGGGGGAACCAAACTGGAGATTAAG*GGGTCTACAAGTGGCTCAGGGA*

*AACCAGGAAGCGGCGAAGGGTCCACAAAGGGC*CAGGTGCAGCTGCAGGAG

TCTGGACCAGGCCTGGTGAAGCCCTCTGAAACTCTGAGTGTCACATGTAC

TGTGAGCGGAGTCTCCCTGCCCGACTACGGCGTGAGTTGGATCAGGCAGC

CCCCTGGGAAAGGACTGGAGTGGCTGGGCGTCATTTGGGGGAGCGAAACC

ACATACTATAACTCAGCCCTGAAGAGCCGGCTGACAATCTCCAAAGACAC

TTCTAAGAATCAGGTGTTTCTGAAAATGTCTAGTCTGACTGCCGCTGATA

CCGCAATCTACTATTGCGCCAAGCACTACTATTACGGCGGCTCCTATGCT

ATGGATTATTGGGGGCAGGGGACTCTGGTCACTGTCTCAAGCTGAT

*CATCATCATCATCATCAT*AA.

In some embodiments, a polynucleotide sequence may be at least about 70%, at least about 75%, at least about 80%, at least about 85%, at least about 90%, at least about 95%, at least about 96%, at least about 97%, at least about 98%, at least about 99%, or about 100% identical to an above-mentioned polynucleotide sequence.

Amino Acid Sequences for the Wild-Type scFv and Four of the Seven Selected Humanized scFvs The below polypeptide sequences are shown in the format of "Leader sequence-VL-Linker-VH-His Tag", i.e., the "Leader sequence" is in bold font, the "Linker" is in italics, and the "His Tag" is in bold italics.

The leader sequence used in each of the below scFvs has the amino acid sequence of MEWTWVFLFLLSVTAGVHS (SEQ ID NO: 6). The linker sequence used in each of the below scFvs has the amino acid sequence of GSTSGSGK-PGSGEGSTKG (SEQ ID NO: 7). The His Tag sequence used in each of the below scFvs has the amino acid sequence of *HHHHHH* (SEQ ID NO: 8)

WT-FMC63-scFv (SEQ ID NO: 9)

MEWTWVFLFLLSVTAGVHSDIQMTQTTSSLSASLGDRVTISCRASQDISKYLNWYQQKPDGTVKLLIYHTSRLH

SGVPSRFSGSGSGTDYSLTISNLEQEDIATYFCQQGNTLPYTFGGGTKLEIT*GSTSGSGKPGSGEGSTKG*EVKL

QESGPGLVAPSQSLSVTCTVSGVSLPDYGVSWIRQPPRKGLEWLGVIWGSETTYYNSALKSRLTIIKDNSKSQV

FLKMNSLQTDDTAIYYCAKHYYYGGSYAMDYWGQGTSVTVSS*HHHHHH*.

The VL sequence for the WT-FMC63-scFV has the amino acid sequence of (SEQ ID NO: 36)

DIQMTQTTSSLSASLGDRVTISCRASQDISKYLNWYQQKPDGTVKLLIYHTSRLHSGVPSRFSGSGSGTDYSLT
ISNLEQEDIATYFCQQGNTLPYTFGGGTKLEIT

The VH sequence for the WT-FMC63-scFV has the amino acid sequence of (SEQ ID NO: 37)

EVKLQESGPGLVAPSQSLSVTCTVSGVSLPDYGVSWIRQPPRKGLEWLGVIWGSETTYYNSALKSRLTIIKDNS
KSQVFLKMNSLQTDDTAIYYCAKHYYYGGSYAMDYWGQGTSVTVSS.

SS-scFv (SEQ ID NO: 10)

MEWTWVFLFLLSVTAGVHSDIQMTQSPSFLSASVGDRVTITCRASQDISKYLNWYQQKPDQAPKLLIKHTSRLH

SGVPSRFSGSGSGTDFTFTISSLQPEDIATYYCQQGNTLPYTFGQGTKLEIK*GSTSGSGKPGSGEGSTKG*EVQL

VESGGGLVQPGRSLRLSCTASGVSLPDYGVSWVRQPPGKGLEWIGVIWGSETTYYNSALKSRFTISRDNSKNTL

YLQMNSLRAEDTAVYYCAKHYYYGGSYAMDYWGQGTLVTVSS*HHHHHH*.

The VL sequence for the SS-scFV has the amino acid sequence of (SEQ ID NO: 11)

DIQMTQSPSFLSASVGDRVTITCRASQDISKYLNWYQQKPDQAPKLLIKHTSRLHSGVPSRFSGSGSGTDFTFT
ISSLQPEDIATYYCQQGNTLPYTFGQGTKLEIK.

The VH sequence for the SS-scFV has the amino acid sequence of
(SEQ ID NO: 12)
EVQLVESGGGLVQPGRSLRLSCTASGVSLPDYGVSWVRQPPKGLEWIGVIWGSETTYYNSALKSRFTISRDNS
KNTLYLQMNSLRAEDTAVYYCAKHYYYGGSYAMDYWGQGTLVTVSS JS-scFv
(SEQ ID NO: 13)
MEWTWVFLFLLSVTAGVHSDIQMTQSPSSLSASVGDRVTITCRASQDISKYLNWYQQKPDQAPKLLIKHTSRLH

SGVPSRFSGSGSGTDYTLTISSLQPEDFATYYCQQGNTLPYTFGQGTKLEIKGSTSGSGKPGSGEGSTKGEVQL

VESGGGLVQPGRSLRLSCTASGVSLPDYGVSWIRQPPKGLEWIGVIWGSETTYYNSALKSRFTISRDNSKNTL

YLQMNSLRAEDTAVYYCAKHYYYGGSYAMDYWGQGTLVTVSS*HHHHHH*.

The VL sequence for the JS-scFV has the amino acid sequence of
(SEQ ID NO: 14)
DIQMTQSPSSLSASVGDRVTITCRASQDISKYLNWYQQKPDQAPKLLIKHTSRLHSGVPSRFSGSGSGTDYTLT
ISSLQPEDFATYYCQQGNTLPYTFGQGTKLEIK.

The VH sequence for the JS-scFV has the amino acid sequence of
(SEQ ID NO: 15)
EVQLVESGGGLVQPGRSLRLSCTASGVSLPDYGVSWIRQPPKGLEWIGVIWGSETTYYNSALKSRFTISRDNS
KNTLYLQMNSLRAEDTAVYYCAKHYYYGGSYAMDYWGQGTLVTVSS.

AS-scFv
(SEQ ID NO: 16)
MEWTWVFLFLLSVTAGVHSDIQMTQSPSTLSASVGDRVTITCRASQDISKYLNWYQQKPDQAPKLLIKHTSRLH

SGVPSRFSGSGSGTDFTFTISSLQPEDIATYYCQQGNTLPYTFGQGTKLEIKGSTSGSGKPGSGEGSTKGQVQL

QESGPGLVKPSGTLSLTCAVSGVSLPDYGVSWIRQPPKGLEWIGVIWGSETTYYNSALKSRVTISRDNSKNTL

YLQMNSLRAEDTAVYYCAKHYYYGGSYAMDYWGQGTLVTVSS*HHHHHH*.

The VL sequence for the AS-scFV has the amino acid sequence of
(SEQ ID NO: 17)
DIQMTQSPSTLSASVGDRVTITCRASQDISKYLNWYQQKPDQAPKLLIKHTSRLHSGVPSRFSGSGSGTDFTFT
ISSLQPEDIATYYCQQGNTLPYTFGQGTKLEIK.

The VH sequence for the AS-scFV has the amino acid sequence of
(SEQ ID NO: 18)
QVQLQESGPGLVKPSGTLSLTCAVSGVSLPDYGVSWIRQPPKGLEWIGVIWGSETTYYNSALKSRVTISRDNS
KNTLYLQMNSLRAEDTAVYYCAKHYYYGGSYAMDYWGQGTLVTVSS.

NS-scFv
(SEQ ID NO: 19)
MEWTWVFLFLLSVTAGVHSDIQMTQSPSSLSASVGDRVTITCRASQDISKYLNWYQQKPGKAVKLLIYHTSRLH

SGVPSRFSGSGSGTDYTLTISSLQPEDIATYFCQQGNTLPYTFGGGTKLEIKGSTSGSGKPGSGEGSTKGQVQL

QESGPGLVKPSETLSVTCTVSGVSLPDYGVSWIRQPPKGLEWLGVIWGSETTYYNSALKSRLTISKDTSKNQV

FLKMSSLTAADTAIYYCAKHYYYGGSYAMDYWGQGTLVTVSS*HHHHHH*.

The VL sequence for the NS-scFV has the amino acid sequence of
(SEQ ID NO: 20)
DIQMTQSPSSLSASVGDRVTITCRASQDISKYLNWYQQKPGKAVKLLIYHTSRLHSGVPSRFSGSGSGTDYTLT
ISSLQPEDIATYFCQQGNTLPYTFGGGTKLEIK.

The VH sequence for the NS-scFV has the amino acid sequence of
(SEQ ID NO: 21)
QVQLQESGPGLVKPSETLSVTCTVSGVSLPDYGVSWIRQPPKGLEWLGVIWGSETTYYNSALKSRLTISKDTS
KNQVFLKMSSLTAADTAIYYCAKHYYYGGSYAMDYWGQGTLVTVSS.

The above-described WT-FMC63-, SS-, JS-, AS-, and NS-scFv amino acid sequences may lack the His Tag (of SEQ ID NO: 8). Accordingly, the scFvs would have the following amino acid sequences:

WT-FMC63-scFv (without His Tag)
(SEQ ID NO: 22)
MEWTWVFLFLLSVTAGVHSDIQMTQTTSSLSASLGDRVTISCRASQDISK

YLNWYQQKPDGTVKLLIYHTSRLHSGVPSRFSGSGSGTDYSLTISNLEQE

DIATYFCQQGNTLPYTFGGGTKLEIT*GSTSGSGKPGSGEGSTKG*EVKLQE

SGPGLVAPSQSLSVTCTVSGVSLPDYGVSWIRQPPRKGLEWLGVIWGSET

TYYNSALKSRLTIIKDNSKSQVFLKMNSLQTDDTAIYYCAKHYYYGGSYA

MDYWGQGTSVTVSS.

SS-scFv (without His Tag)
(SEQ ID NO: 23)
MEWTWVFLFLLSVTAGVHSDIQMTQSPSFLSASVGDRVTITCRASQDISK

YLNWYQQKPDQAPKLLIKHTSRLHSGVPSRFSGSGSGTDFTFTISSLQPE

-continued

DIATYYCQQGNTLPYTFGQGTKLEIK*GSTSGSGKPGSGEGSTKG*EVQLVE

SGGGLVQPGRSLRLSCTASGVSLPDYGVSWVRQPPGKGLEWIGVIWGSET

TYYNSALKSRFTISRDNSKNTLYLQMNSLRAEDTAVYYCAKHYYYGGSYA

MDYWGQGTLVTVSS

JS-scFv (without His Tag)
(SEQ ID NO: 24)
MEWTWVFLFLLSVTAGVHSDIQMTQSPSSLSASVGDRVTITCRASQDISK

YLNWYQQKPDQAPKLLIKHTSRLHSGVPSRFSGSGSGTDYTLTISSLQPE

DFATYYCQQGNTLPYTFGQGTKLEIK*GSTSGSGKPGSGEGSTKG*EVQLVE

SGGGLVQPGRSLRLSCTASGVSLPDYGVSWIRQPPGKGLEWIGVIWGSET

TYYNSALKSRFTISRDNSKNTLYLQMNSLRAEDTAVYYCAKHYYYGGSYA

MDYWGQGTLVTVSS.

AS-scFv (without His Tag)
(SEQ ID NO: 25)
MEWTWVFLFLLSVTAGVHSDIQMTQSPSTLSASVGDRVTITCRASQDISK

YLNWYQQKPDQAPKLLIKHTSRLHSGVPSRFSGSGSGTDFTFTISSLQPE

DIATYYCQQGNTLPYTFGQGTKLEIK*GSTSGSGKPGSGEGSTKG*QVQLQE

SGPGLVKPSGTLSLTCAVSGVSLPDYGVSWIRQPPGKGLEWIGVIWGSET

TYYNSALKSRVTISRDNSKNTLYLQMNSLRAEDTAVYYCAKHYYYGGSYA

MDYWGQGTLVTVSS.

NS-scFv (without His Tag)
(SEQ ID NO: 26)
MEWTWVFLFLLSVTAGVHSDIQMTQSPSSLSASVGDRVTITCRASQDISK

YLNWYQQKPGKAVKLLIYHTSRLHSGVPSRFSGSGSGTDYTLTISSLQPE

DIATYFCQQGNTLPYTFGGGTKLEIK*GSTSGSGKPGSGEGSTKG*QVQLQE

SGPGLVKPSETLSVTCTVSGVSLPDYGVSWIRQPPGKGLEWLGVIWGSET

TYYNSALKSRLTISKDTSKNQVFLKMSSLTAADTAIYYCAKHYYYGGSYA

MDYWGQGTLVTVSS.

In some embodiments, a polypeptide sequence may be at least about 70%, at least about 75%, at least about 80%, at least about 85%, at least about 90%, at least about 95%, at least about 96%, at least about 97%, at least about 98%, at least about 99%, or about 100% identical to any one of the above-mentioned polypeptide sequences.

A humanized antibody, e.g., scFv, has a VL region which differs from SEQ ID NO: 36 by at least one amino acid, e.g., 1, 2, 3, 4, 5, 6, 7, 8, 9, 10, 11, 12, 13, 14, 15, 16, 17, 18, 19, 20 21, 22, 23, 24, 25, or more amino acids. For example, a humanized antibody, e.g., scFv, may have a VL region differs from SEQ ID NO: 36 by having a Ser at position 7, Pro at position 8, Val at position 15, Thr at position 22, Gln at position 41, Lys at position 42, Gln at position 42, Ala at position 43, Pro at position 44, Lys at position 49, Thr at position 72, Ser at position 77, Gln at position 79, Pro at position 80, Phe at position 83, Tyr at position 87, Gln at position 100, and/or Lys at position 107. In some embodiments, the humanized antibody, e.g., scFv, may have a VL region differs from SEQ ID NO: 36 by having a Ser at position 7, Pro at position 8, Val at position 15, Thr at position 22, Gln at position 42, Ala at position 43, Pro at position 44, Lys at position 49, Thr at position 72, Ser at position 77, Gln at position 79, Pro at position 80, Phe at position 83, Tyr at position 87, Gln at position 100, and/or Lys at position 107. In other embodiments, the humanized antibody, e.g., scFv, may have a VL region differs from SEQ ID NO: 36 by having a Ser at position 7, Pro at position 8, Val at position 15, Thr at position 22, Gln at position 41, Lys at position 42, Ala at position 43, Thr at position 72, Ser at position 77, Gln at position 79, Pro at position 80, and Lys at position 107.

A humanized antibody, e.g., scFv, has a VH region which differs from SEQ ID NO: 37 by at least one amino acid, e.g., 1, 2, 3, 4, 5, 6, 7, 8, 9, 10, 11, 12, 13, 14, 15, 16, 17, 18, 19, 20 21, 22, 23, 24, 25, or more amino acids. For example, a humanized antibody, e.g., scFv, may have a VH region differs from SEQ ID NO: 37 by having a Gln at position 1, Gln at position 3, Val at position 5, Gly at position 9, Lys at position 13, Gln at position 13, Gly at position 15, Arg at position 16, Thr at position 16, Thr at position 17, Arg at position 19, Leu at position 20, Ser at position 21, Ala at position 24, Gly at position 42, Ile at position 48, Phe at position 67, Ser at position 70, Arg at position 71, Thr at position 73, Asn at position 76, Thr at position 77, Leu at position 78, Tyr at position 79, Gln at position 81, Ser at position 83, Thr at position 86, Arg at position 86, Ala at position 87, Glu at position 88, Ala at position 88, Val at position 92, and/or Leu at position 115. In some embodiments, the humanized antibody, e.g., scFv, may have a VH region differs from SEQ ID NO: 37 by having a Gln at position 3, Val at position 5, Gly at position 9, Gln at position 13, Gly at position 15, Arg at position 16, Arg at position 19, Leu at position 20, Ser at position 21, Ala at position 24, Gly at position 42, Ile at position 48, Phe at position 67, Ser at position 70, Arg at position 71, Asn at position 76, Thr at position 77, Leu at position 78, Tyr at position 79, Gln at position 81, Arg at position 86, Ala at position 87, Glu at position 88, Val at position 92, and/or Leu at position 115. In other embodiments, the humanized antibody, e.g., scFv, may have a VH region differs from SEQ ID NO: 37 by having a Gln at position 1, Gln at position 3, Lys at position 13, Thr at position 16, Thr at position 17, Gly at position 42, Ser at position 70, Thr at position 73, Asn at position 76, Ser at position 83, Thr at position 86, Ala at position 87, Ala at position 88, and/or Leu at position 115.

In some embodiments, the antigen binding molecule binds a target antigen (e.g., human CD19) with a $K_D$ of less than $1\times10^{-6}$ M, less than $1\times10^{-7}$ M, less than $1\times10^{-8}$ M, or less than $1\times10^{-9}$ M. In some embodiments, the antigen binding molecule binds a target antigen (e.g., human CD19) with a $K_D$ of about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, or about $9\times10^{-9}$ M. In certain embodiments, the $K_D$ is calculated as the quotient of $k_{off}/k_{on}$, and the $k_{on}$ and $k_{off}$ are determined using a monovalent antibody, such as a Fab fragment, as measured by, e.g., BIAcore® surface plasmon resonance technology. In other embodiments, the $K_D$ is calculated as the quotient of $k_{off}/k_{on}$, and the $k_{on}$ and $k_{off}$ are determined using a bivalent antibody, such as a Fab fragment, as measured by, e.g., BIAcore® surface plasmon resonance technology.

In some embodiments, the antigen binding molecule binds a target antigen (e.g., human CD19) with an association rate ($k_{on}$) of less than $1\times10^{-4}$ M$^{-1}$ s$^{-1}$, less than $2\times10^{-4}$ M$^{-1}$ s$^{-1}$, less than $3\times10^{-4}$ M$^{-1}$ s$^{-1}$, less than $4\times10^{-4}$ M$^{-1}$ s$^{-1}$, less than $5\times10^{-4}$ M$^{-1}$ s$^{-1}$, less than $6\times10^{-4}$ M$^{-1}$ s$^{-1}$, less than $7\times10^{-4}$ M$^{-1}$ s$^{-1}$, less than $8\times10^{-4}$ M$^{-1}$ s$^{-1}$, less than $9\times10^{-4}$ M$^{1}$ s$^{-1}$, less than $1\times10^{-5}$ M$^{-1}$ s$^{-1}$, less than $2\times10^{-5}$ M$^{-1}$ s$^{-1}$, less than $3\times10^{-5}$ M$^{-1}$ s$^{-1}$, less than $4\times10^{-5}$ M$^{-1}$ s$^{-1}$, less than $5 \times 10^{-5}$ M$^{-1}$ s$^{-1}$, less than $6 \times 10^{-5}$ M$^{-1}$ s$^{-1}$, less than $7 \times 10^{-5}$ M$^{-1}$ s$^{-1}$, less than $8 \times 10^{-5}$ M$^{-1}$ s$^{-1}$, less than $9 \times 10^{-5}$ M$^{-1}$ s$^{-1}$, less than $1 \times 10^{-6}$ M$^{-1}$ s$^{-1}$, less than $2 \times 10^{-6}$ M$^{-1}$ s$^{-1}$, less than $3 \times 10^{-6}$ M$^{-1}$ s$^{-1}$, less than $4 \times 10^{-6}$ M$^{-1}$ s$^{-1}$, less than $5 \times 10^{-6}$ M$^{-1}$ s$^{-1}$, less than $6 \times 10^{-6}$ M$^{-1}$ s$^{-1}$, less than $7 \times 10^{-6}$ M$^{-1}$ s$^{-1}$, less than $8 \times 10^{-6}$ M$^{-1}$ s$^{-1}$, less than $9 \times 10^{-6}$ M$^{-1}$ s$^{-1}$, or less than $1 \times 10^{-7}$ M$^{-1}$ s$^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the antigen binding molecule binds a target antigen (e.g., human CD19) with an dissociation rate ($k_{off}$) of less than $1 \times 10^{-2}$ s$^{-1}$, less than $2 \times 10^{-2}$ s$^{-1}$, less than $3 \times 10^{-2}$ s$^{-1}$, less than $4 \times 10^{-2}$ s$^{-1}$, less than $5 \times 10^{-2}$ s$^{-1}$, less than $6 \times 10^{-2}$ s$^{-1}$, less than $7 \times 10^{-2}$ s$^{-1}$, less than $8 \times 10^{-2}$ s$^{-1}$, less than $9 \times 10^{-2}$ s$^{-1}$, less than $1 \times 10^{-3}$ s$^{-1}$, less than $2 \times 10^{-3}$ s$^{-1}$, less than $3 \times 10^{-3}$ s$^{-1}$, less than $4 \times 10^{-3}$ s$^{-1}$, less than $5 \times 10^{-3}$ s$^{-1}$, less than $6 \times 10^{-3}$ s$^{-1}$, less than $7 \times 10^{-3}$ s$^{-1}$, less than $8 \times 10^{-3}$ s$^{-1}$, less than $9 \times 10^{-3}$ s$^{-1}$, less than $1 \times 10^{-4}$ s$^{-1}$, less than $2 \times 10^{-4}$ s$^{-1}$, less than $3 \times 10^{-4}$ s$^{-1}$, less than $4 \times 10^{-4}$ s$^{-1}$, less than $5 \times 10^{-4}$ s$^{-1}$, less than $6 \times 10^{-4}$ s$^{-1}$, less than $7 \times 10^{-4}$ s$^{-1}$, less than $8 \times 10^{-4}$ s$^{-1}$, less than $9 \times 10^{-4}$ s$^{-1}$, less than $1 \times 10^{-4}$ s$^{-1}$, or less than $5 \times 10^{-4}$ s$^{-1}$ In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

In some embodiments, the polynucleotide encodes a TCR, wherein the TCR further comprises a fourth complementarity determining region (CDR4). In certain embodiments, the polynucleotide encodes a TCR, wherein the TCR further comprises a constant region. In some embodiments, the constant region is selected from a constant region of IgG1, IgG2, IgG3, IgG4, IgA, IgD, IgE, and IgM.

I.B. Costimulatory Domains

Chimeric antigen receptors incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). An exemplary costimulatory protein has the amino acid sequence of a costimulatory protein found naturally on T cells. The complete native amino acid sequence of this costimulatory protein is described in NCBI Reference Sequence: NP_006130.1.

The polynucleotide and polypeptide sequences of other costimulatory domains are known in the art. In some embodiments, the polynucleotide encoding a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art. In some embodiments, the polypeptide sequence of a costimulatory domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art.

I.B.1 Extracellular or "Hinge" Domains

In one embodiment, a CAR or TCR of the instant disclosure comprises an "extracellular" or "hinge" or "spacer" domain or region, which terms are used interchangeably herein. In another embodiment, an extracellular domain is from or derived from (e.g., comprises all or a fragment of) CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158FI (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. An "extracellular" or "hinge" or "spacer" domain or region can be derived either from a natural or from a synthetic source. The polynucleotide and polypeptide sequences of these hinge domains are known in the art.

In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art.

In some embodiments, a hinge domain is positioned between an antigen binding domain (e.g., an scFv) and a transmembrane domain. In this orientation, the hinge domain provides distance between the antigen binding domain and the surface of a cell membrane through which the CAR is expressed. In some embodiments, a hinge domain is from or derived from an immunoglobulin. In some embodiments, a hinge domain is selected from the hinge regions of IgG1, IgG2, IgG3, IgG4, IgA, IgD, IgE, and IgM, or a fragment thereof. In other embodiments, a hinge domain comprises, is from, or is derived from the hinge region of CD8 alpha. In some embodiments a hinge domain comprises, is from, or is derived from the hinge region of CD28. In some embodiments, a hinge domain comprises a fragment of the hinge region of CD8 alpha or a fragment of the hinge region of CD28, wherein the fragment is anything less than the whole hinge region In some embodiments, the fragment of the CD8 alpha hinge region or the fragment of the CD28 hinge region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge region, or of the CD28 hinge region.

I.B.2 Transmembrane Domains

The costimulatory domain for the CAR or TCR of the invention can further comprise a transmembrane domain and/or an intracellular signaling domain. The transmembrane domain can be designed to be fused to the extracellular domain of the CAR. It can similarly be fused to the intracellular domain of the CAR. In one embodiment, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain can be derived either from a natural or from a synthetic source. Where the source is natural, the domain can be derived from any membrane-bound or transmembrane protein. Transmembrane regions of particular use in this invention can be derived from (i.e., comprise) 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. The polynucleotide and polypeptide sequences of these transmembrane domains are known in the art.

In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art.

Optionally, short linkers can form linkages between any or some of the extracellular, transmembrane, and intracellular domains of the CAR.

I.B.3. Intracellular (Signaling) Domains

The intracellular (signaling) domain of the engineered T cells of the invention can provide signaling to an activating domain, which then activates at least one of the normal effector functions of the immune cell. Effector function of a T cell, for example, can be cytolytic activity or helper activity including the secretion of cytokines.

In certain embodiments, suitable intracellular signaling domains include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that specifically binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof. The polynucleotide and polypeptide sequences of these intracellular signaling domains are known in the art.

In some embodiments, the polynucleotide encoding an intracellular signaling domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art. In some embodiments, the polypeptide sequence of an intracellular signaling domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art.

I.C. Activating Domains

CD3 is an element of the T cell receptor on native T cells, and has been shown to be an important intracellular activating element in CARs. In some embodiments, the CD3 is CD3-zeta or CD3-epsilon, the polynucleotide and polypeptide sequences of each of which are known in the art.

In some embodiments, the polynucleotide encoding an activating domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art. In some embodiments, the polypeptide sequence of an activating domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art.

I.D. Switch Domains

It will be appreciated that adverse events may be minimized by transducing the immune cells (containing one or more CARs or TCRs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after, or at the same time, as the cells are transduced with the CAR construct of the present invention. Additional methods for introducing suicide genes and/or "on" switches include TALENS, zinc fingers, RNAi, siRNA, shRNA, antisense technology, and other techniques known in the art.

In accordance with the invention, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

I.E. Leader Peptides or Leader Sequences

In some embodiments, the polynucleotide of the present invention encodes a CAR or a TCR, which can further comprise a leader peptide (also referred to herein as a "signal peptide" or "leader sequence"). In certain embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MEWTWVFL-FLLSVTAGVHS (SEQ ID NO: 6) or MALPVTALLL-PLALLLHAARP (SEQ ID NO: 35). In some embodiments, the leader peptide comprises the amino acid sequence of SEQ ID NO: 6 or SEQ ID NO: 35.

The polynucleotide and polypeptide sequences of other leader peptides are known in the art.

In some embodiments, the polynucleotide encoding a leader peptide comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art In some embodiments, the polypeptide sequence of a leader peptide comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art.

In some embodiments, the polynucleotide of the present invention encodes a CAR or a TCR, wherein the CAR or the TCR comprises a leader peptide (P), an antigen binding molecule (B), a costimulatory protein's extracellular domain (E), a transmembrane domain (T), a costimulatory region (C), and an activation domain (A), wherein the CAR is configured according to the following: P B E T C A. In some embodiments, the antigen binding molecule comprises a VH and a VL, wherein the CAR is configured according to the following: P-VH-VL-E-T-C-A or P-VL-VH-E-T-C-A. In some embodiments, the VH and the VL are connected by a linker (L), wherein the CAR is configured according to the following, from N-terminus to C-terminus: P-VH-L-VL-E-T-C-A or P-VH-L-VL-E-T-C-A.

In some embodiments, the polynucleotide of the present invention encodes a CAR or TCR, wherein the CAR or TCR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence for a CAR or TCR known in the art. See, e.g., U.S. 62/470,703 and U.S. 62/317,258.

II. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding a CAR or a TCR comprising the antigen-binding domain as described herein.

Any vector known in the art can be suitable for the present invention. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are cells comprising a polynucleotide or a vector of the present invention. In some embodiments, the present invention is directed to cells, e.g., in vitro cells, comprising a polynucleotide encoding a CAR or a comprising the antigen-binding domain as described herein. In other embodiments, the present invention is directed to cells, e.g., in vitro cells, comprising a polypeptide encoded by a CAR or a TCR comprising the antigen-binding domain as described herein.

Any cell may be used as a host cell for the polynucleotides, the vectors, or the polypeptides of the present invention. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof.

The cell of the present invention may be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the Cobe™ 2991 cell processor, the Baxter CytoMate™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL™ gradient. In some embodiments, a specific subpopulation of T cells, such as $CD4^+$, $CD8^+$, $CD28^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD8, CD11b, CD14, CD16, CD20, and HLA-DR. In certain embodiments, flow cytometry and cell sorting are used to isolate cell populations of interest for use in the present invention.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CCR7, CD3, CD28, CD45RO, CD62L, and CD127 and are negative for granzyme B. In some embodiments, central memory T cells are $CD8^+$, $CD45RO^+$, and $CD62L^+$ T cells. In some embodiments, effector T cells are negative for CCR7, CD28, CD62L, and CD127 and positive for granzyme B and perforin. In certain embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynaheads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Other aspects of the present invention are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR comprising the antigen-binding domain as described herein. In another embodiment, the composition comprises a CAR or a TCR comprising the antigen-binding domain, as described herein, encoded by a polynucleotide of the present invention. In another embodiment, the composition comprises a T cell comprising a CAR or a TCR comprising the antigen-binding domain as described herein.

III. Methods of the Invention

Another aspect of the invention is directed to a method of making a cell expressing a CAR or a TCR comprising a transduced cell with a polynucleotide disclosed herein under suitable conditions. In some embodiments, the method comprises transducing a cell with a polynucleotide encoding a CAR or a TCR, as disclosed herein. In some embodiments, the method comprises transducing a cell with a vector comprising the polynucleotide encoding a CAR or a TCR.

Another aspect of the present invention is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR disclosed herein. In another embodiment, the method comprises administering to a subject an effective amount of a cell comprising a vector comprising a polynucleotide encoding a CAR or a TCR disclosed herein. In another embodiment, the method comprises administering to a subject an effective amount of a cell comprising a CAR or a TCR encoded by a polynucleotide disclosed herein.

Another aspect of the present invention is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR, wherein the CAR or the TCR comprises the antigen-binding domain as described herein. In some embodiments, the target cell is a tumor cell.

Another aspect of the present invention is directed to a method for treating or preventing a malignancy, said method comprising administering to a subject in need thereof an effective amount of at least one immune cell, wherein the immune cell comprises at least one CAR or TCR, and wherein the CAR or the TCR comprises the antigen-binding domain as described herein.

Another aspect of the present invention is directed to a method of treating a cancer in a subject in need thereof comprising administering to the subject a polynucleotide, a vector, a CAR or a TCR, a cell, or a composition disclosed herein. In one embodiment, the method comprises administering a polynucleotide encoding a CAR or a TCR. In another embodiment, the method comprises administering a vector comprising a polynucleotide encoding a CAR or a TCR. In another embodiment, the method comprises administering a CAR or a TCR encoded by a polynucleotide disclosed herein. In another embodiment, the method comprises administering a cell comprising the polynucleotide, or a vector comprising the polynucleotide, encoding a CAR or a TCR.

In some embodiments, the methods of treating a cancer in a subject in need thereof comprise a T cell therapy. In one embodiment, the T cell therapy of the present invention is engineered Autologous Cell Therapy (eACT™). According to this embodiment, the method can include collecting blood cells from the patient. The isolated blood cells (e.g., T cells) can then be engineered to express a CAR or a TCR of the present invention. In a particular embodiment, the CAR T cells or the TCR T cells are administered to the patient. In some embodiments, the CAR T cells or the TCR T cells treat a tumor or a cancer in the patient. In one embodiment the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$ cells, or at least about $10^{10}$. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the CAR T cells or the TCR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

IV. Cancer Treatment

The methods of the invention can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

Cancers that may be treated include B-cell lymphomas. In certain embodiments, the B-cell lymphomas Acute Lymphoblastic Leukemia (ALL), AIDS-related lymphoma, ALK-positive large B-cell lymphoma, Burkitt's lymphoma, Chronic lymphocytic leukemia, CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia, or a combination thereof. In one embodiment, the B-cell lymphoma is Acute Lymphoblastic Leukemia (ALL), Chronic lymphocytic leukemia, CLL), Diffuse large B-cell lymphoma (DLBCL), Follicular lymphoma, Mantle cell lymphoma (MCL), Marginal zone B-cell lymphoma (MZL), Mucosa-Associated Lymphatic Tissue lymphoma (MALT), and Non-Hodgkin's lymphoma. In one embodiment, the B-cell lymphoma is Non-Hodgkin's lymphoma.

In some embodiments, the methods further comprise administering a chemotherapeutic.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered prior to, in conjunction with, and/or subsequent to any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine resume; nitrogen mustards such as chlorambucil, chlornaphazine, chlorpromazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In certain embodiments, compositions comprising CAR- and/or TCR-expressing immune effector cells disclosed herein may be administered prior to, in conjunction with, and/or subsequent to CHOP. CHOP consists of (C)yclophosphamide, an alkylating agent which damages DNA by binding to it and causing the formation of cross-links; (H)ydroxydaunorubicin (also called doxorubicin or adriamycin), an intercalating agent which damages DNA by inserting itself between DNA bases; (O)ncovin (vincristine), which prevents cells from duplicating by binding to the protein tubulin; and (P)rednisone or (P)rednisolone, which are corticosteroids.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

Additional therapeutic agents suitable for use in combination with the invention include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

Additional therapeutic agents suitable for use in the present invention include radioactive atoms. Examples of such radioactive atoms include $^{131}$I, $^{90}$Y, $^{212}$Bi, $^{186}$Re, $^{221}$At, $^{99m}$Tc and mixtures thereof. However, other radioactive atoms may also be utilized as is known in the art.

In additional embodiments, the composition comprising CAR- and/or TCR-expressing T cells, a conjugate comprising an scFV, or an scFV itself, are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

V. Conjugates

An antigen binding domain of the present invention (e.g., an anti-human CD19 scFV), can be conjugated (e.g., linked to) to a therapeutic agent (e.g., chemotherapeutic agent and radioactive atom) as described herein.

Techniques for conjugating such therapeutic agents to antibodies, e.g., scFvs, are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery (2nd Ed.)*, Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., *Immunol. Rev.*, 62:119-58, 1982 Each of the aforementioned references are incorporated by reference in its entirety.

VI. Antibody Humanizing

Antibody humanization is the process of replacing non-human antibody, e.g., scFv, frameworks with human ones. Successful antibody humanization depends on maintaining the affinity after replacing residues. In some embodiments, humanized antibodies are antibody molecules in which at least part of the sequence of both the light chain and the heavy chain arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies and Cancer Therapy, Alan R. Liss, Inc., pp. 77-96) Human monoclonal antibodies may be produced using human hybridomas (see Cote, et al., 1983. Proc Natl Acad Sci USA 80: 2026-2030) or by transforming human B cells with Epstein Barr Virus in vitro (see Cole, et al., 1985 In: Monoclonal Antibodies and Cancer Therapy, Alan R. Liss, Inc., pp. 77-96).

Additionally, human antibodies, e.g., scFvs, may be produced using additional techniques, including phage display libraries (See Hoogenboom and Winter, J. Mol. Biol., 227: 381 (1991); Marks et al., J. Mol. Biol., 222:581 (1991)). Similarly, human antibodies may be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described in U.S. Pat. Nos. 5,545,807; 5,545, 806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

GenScript® provides a method humanizing antibodies. The method follows Combining CDR-grafting, structure-based back mutation method, and FAst Screening for Expression level, Biophysical properties, and Affinity technology (FASEBA) which generates a humanized antibody, e.g., scFv, with affinity and optimized properties. FASEBA technology is used to optimize properties of the humanized antibody, such as expression level and thermo-stability, which are important for optimal manufacturing and the in vivo behavior. Additional details of the method of GenScript® is found at the World Wide Web (www) at genscript.com/Antibody-Humanization.html. The contents of which, as available at the present application's disclosure, are incorporated by reference in its entirety.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The present invention is further illustrated by the following examples which should not be construed as further limiting. The contents of all references cited throughout this application are expressly incorporated herein by reference.

EXAMPLES

Example 1: Humanization of the scFvs of the FMC63 Antibody

The aim of this example was to humanize an anti-CD19 mouse monoclonal antibody (mAb) clone FMC63 using CDR grafting plus back mutation without sacrificing the binding affinity of the parental (wild type) antibody.
Binding Validation of Antigen Cell and Reference Antibody Raji (*Homo sapiens* Burkitt's lymphoma) cells were cultured and harvested by centrifugation. About $3 \times 10^5$ cells per well were washed with PBS twice and incubated in 200 µl of serial dilutions of reference antibodies (FMC63: a mouse anti-human B cell (CD19) IgG antibody) for 30 minutes at 4° C. After washing with PBS, secondary antibody (5 µg/ml goat anti-mouse IgG [FITC]) was added to the cells and incubated for 30 minutes at 4° C. After washing with PBS, cells were analyzed for binding EC50 by using FACSCalibur™ (BD Bioscience, San Jose, Calif.) and FlowJo software (Ashland, Oreg.).

The reference antibody (FMC63) bound to Raji cells, but not to Eol-1 cells (*Homo sapiens* acute myeloid (eosinophilic) leukemia) (data not shown).
Generation of Humanized FMC63 Libraries The combinatorial humanized back mutation (BM) screening library for the heavy and light chains for FMC63 was designed. The construction of library was carried out following GenScript's standard operating procedures.
Isolation of Humanized FMC63 scFvs from Phage Display Library The humanized scFv phage display library obtained from the above-mentioned humanized library was panned against Raji (*Homo sapiens* Burkitt's lymphoma) cells. The input phage particles were pre-incubated with and without Eol-1 (*Homo sapiens* acute myeloid (eosinophilic) leukemia) cells, and the bound phage was eluted by TEA with prior competition elution by wild type antibody, to get diversified and high-affinity binders.

Individual output phage clones were amplified in 96-deep-well plates and the amplified phage were assayed by cell based ELISA and flow cytometry validation. Bound phage was probed by a HRP/Anti-M13 monoclonal antibody.

The panning ended when a good percentage of phage clones were found to bind with Raji cells, but not to Eol-1 cells. Panning and phage ELISA were carried out following GenScript's standard operating procedures.
Fast Screening for Expression, Biophysical-Properties, and Affinity (FASEBA)

Selected output phage was used to infect exponentially growing TG1 (Phage-display competent) cells. Transfected cells were grown, from which dsDNAs were extracted. Humanized scFv fragment was digested from the double strand phagemid and inserted in the pFASEBA vector for the screening of the best humanized antibody clones.

Individual clones were expressed in 96-deep-well plates and the crude protein secreted by *E. coli* to the medium was assayed by ELISA against BSA and FACS validation against Raji cells for the assessment of expression and binding activity, respectively.
Construction and Production of Humanized FMC63 scFvs The DNA sequences encoding the humanized heavy and light chains for FMC63 (mouse anti-human B cells (CD19) IgG antibody) were synthesized and inserted into pTT5 expression vector to construct scFv-(single chain fragment variable) expressing plasmids. Expression of humanized antibodies was conducted in 100 ml HEK293 cell culture and the supernatants were purified with Ni-chelating affinity column. The purified antibody was buffer-exchanged into PBS using PD-10 desalting column. The concentration and purity of the purified proteins were determined by OD280 and SDS-PAGE, respectively.
Flow Cytometry Titration of Humanized FMC63 scFvs For affinity ranking of humanized FMC63 antibodies to Raji cells, the purified antibodies were subject to flow cytometry titration. In brief, Raji cells were cultured and harvested by centrifugation. About $3 \times 10^5$ cells per well were washed with PBS twice and incubated in 200 µl of serial dilutions of scFvs for 30 minutes at 4° C. After washing with PBS, secondary antibody (5 µg/ml His Tag antibody [FITC]) was added to the cells and incubated for 30 minutes at 4° C. After washing with PBS, cells were analyzed for binding EC50 by using FACSCalibur™ and FlowJo software.
Isolation of Humanized FMC63 scFvs Clones from Phage Display Library Panning of humanized scFv phage library pre-incubated with and without Eol-1 cells were performed (Table 4).

TABLE 4

Details of cell panning and phage ELISA validations

| Round | Antigen | Input (pfu) | Output (pfu) | Positive rate of Phage ELISA (S/N > 3) |
|---|---|---|---|---|
| $1^{st}$ | $1 \times 10^7$ Raji cell (pre-incubated with Eol-1) | $3 \times 10^{11}$ | $2.30 \times 10^5$ | 14.6% |
| $2^{nd}$ | $1 \times 10^7$ Raji cell (pre-incubated with Eol-1) | $3 \times 10^{11}$ | $1.58 \times 10^6$ | 64.3% |
| $1^{st}$ | $1 \times 10^7$ Raji cell | $3 \times 10^{11}$ | $3.18 \times 10^5$ | 6.20% |
| $2^{nd}$ | $1 \times 10^7$ Raji cell | $3 \times 10^{11}$ | $4.24 \times 10^5$ | 60.4% |

The positive rate (the number of antigen-specific humanized clones over the total number of randomly picked clones) of the second round was ~40%. The results of cell-based ELISA against Raji and Eol-1 cell were consistently observed followed by validations with flow cytometry.

FASEBA Screening

DNAs encoding scFv fragments of the second output phage were amplified and inserted into pFASEBA vector for screening of the lead antibodies. Individual FASEBA library clones were inoculated and induced for expression in 96-deep-well plates. FACS screening was performed to isolate scFvs which recognize Raji cell specifically.

According to the results, seven clones (named RS, CS, BS, SS, JS, AS, and NS) were selected for expression, purification and affinity measurement.

Expression and Purification of Humanized FMC63 scFvs

The above-mentioned seven humanized scFvs and wild-type scFvs were expressed in 100 ml HEK293 cells and purified by NTA-Ni resin. The purity of each scFv was over 90% as evaluated by SDS-PAGE.

Flow Cytometry Titration of Humanized FMC63 scFvs

The binding of humanized scFvs with Raji cells was first investigated by FACS starting with 3 µM purified antibodies in use. Positive binding signal were consistently observed for the seven above-mentioned humanized scFv clones during two rounds of flow cytometry.

Figure 3A:
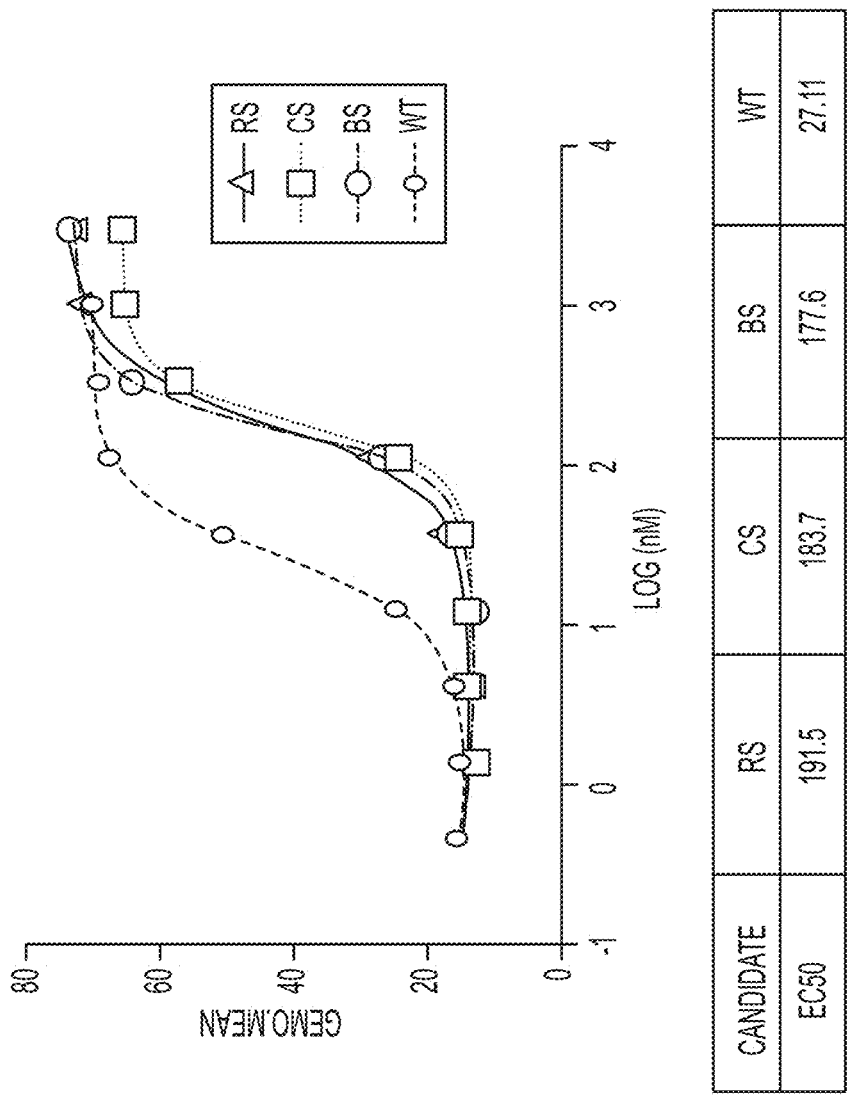
FIG. 3A and FIG. 3B are graphs showing flow cytometry data for seven selected humanized scFvs for binding to Raji (CD19+*Homo sapiens* Burkitt's lymphoma) cells. RS, CS, BS, SS, JS, AS, AS-R, and NS represent inventor's internal naming convention for the humanized antibodies; WT represents wild type.
Figure 3B:
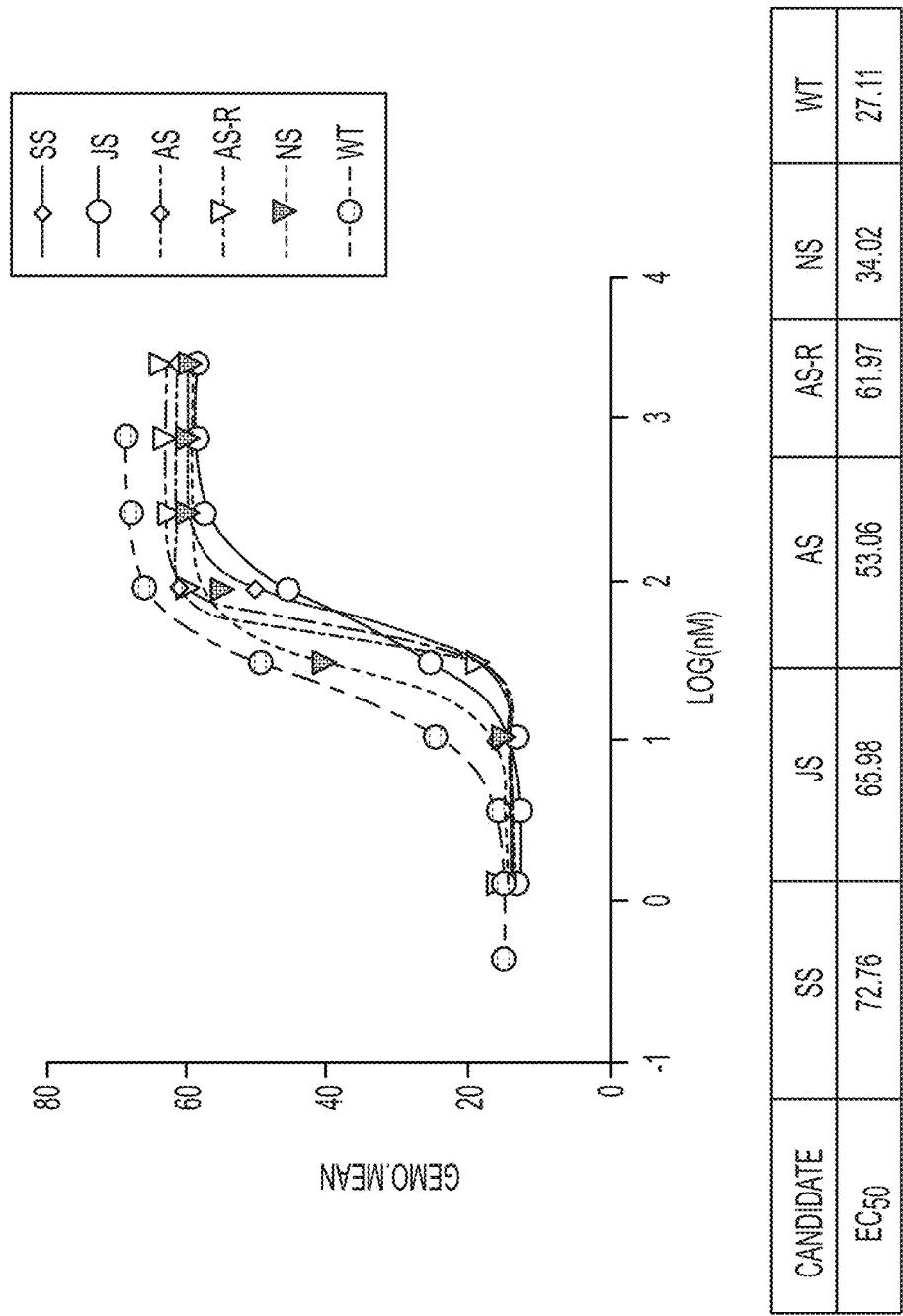

Finally, these seven humanized scFvs were selected for analysis by flow cytometry. The geometric means and EC50 of the seven selected humanized antibodies were shown in FIG. 3A and FIG. 3B and Table 5. Of note, the EC50 of scFv clones SS, JS, AS/AS-R, and NS were at 72.76 nM, 65.98 nM, 53.06/61.97 nM and 34.02 nM respectively, comparable with 27.11 nM of wild type antibody.

TABLE 5

The geometric means of seven selected humanized scFvs by FACS titration

| log(nM) | RS | CS | BS | SS | JS | AS | AS-R | NS | WT |
|---|---|---|---|---|---|---|---|---|---|
| 3.477121 | 72.7 | 65.8 | 73.3 | 62 | 60.2 | 62.7 | 65.2 | 60.7 | / |
| 3 | 72.5 | 65.4 | 70.9 | 61.7 | 59.7 | 62.4 | 64.5 | 61.9 | 70.3 |
| 2.522879 | 58.3 | 57.4 | 64.1 | 60.4 | 58.9 | 63.9 | 64.2 | 61.6 | 69.4 |
| 2.045758 | 29.3 | 23.9 | 26.8 | 51.4 | 46.6 | 62.4 | 61.6 | 56.3 | 67.7 |
| 1.568636 | 18.1 | 14.7 | 16.9 | 19.3 | 25.7 | 19.4 | 18.9 | 41.2 | 50.8 |
| 1.091515 | 14.1 | 13.9 | 12.7 | 14.6 | 13.6 | 14.5 | 16.1 | 15.1 | 24.9 |
| 0.614394 | 13.2 | 13.6 | 14.7 | 13.9 | 13.3 | 14 | 13.4 | 15.5 | 15.7 |
| 0.137273 | 13.7 | 12.4 | 15.3 | 13.9 | 13.4 | 14.2 | 14.9 | 15.7 | 15.5 |
| −0.33985 | / | / | / | / | / | / | / | / | 15.4 |
| EC50 | 191.5 | 183.7 | 177.6 | 72.76 | 65.98 | 53.06 | 61.97 | 34.02 | 27.11 |

Characterization of Four of the Seven Selected scFVs.

Nucleotide sequences encoding the wild-type scFv and four of the seven selected humanized scFvs are described above in the Detailed Description. Likewise, amino acid sequences for the wild-type scFv and four of the seven selected humanized scFvs are described above in the Detailed Description.

Four humanized scFvs (clones named SS, JS, AS, and NS), which had comparable binding EC50 to the wild type scFv, were chosen for further characterization.

Figure 4A:
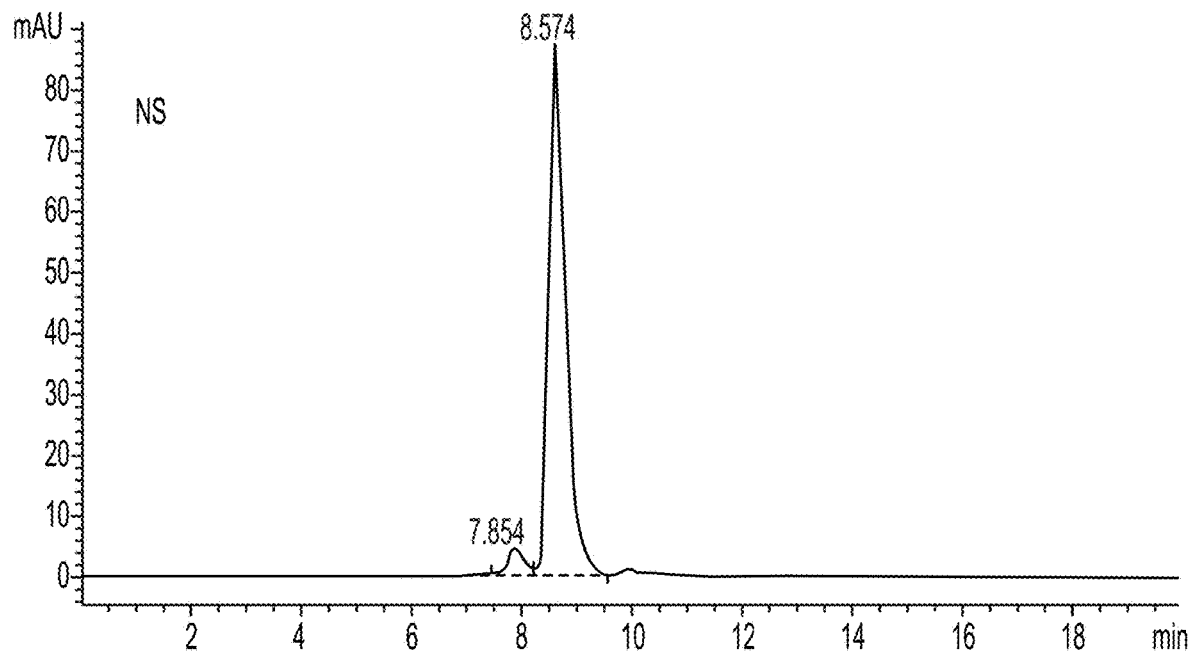
FIG. 4A to FIG. 4D are graphs showing size-exclusion chromatography (SEC) analyses of the NS, SS, JS, and AS humanized scFVs. This assay reflects the soluble aggregation propensity of these antibodies.
Figure 4B:
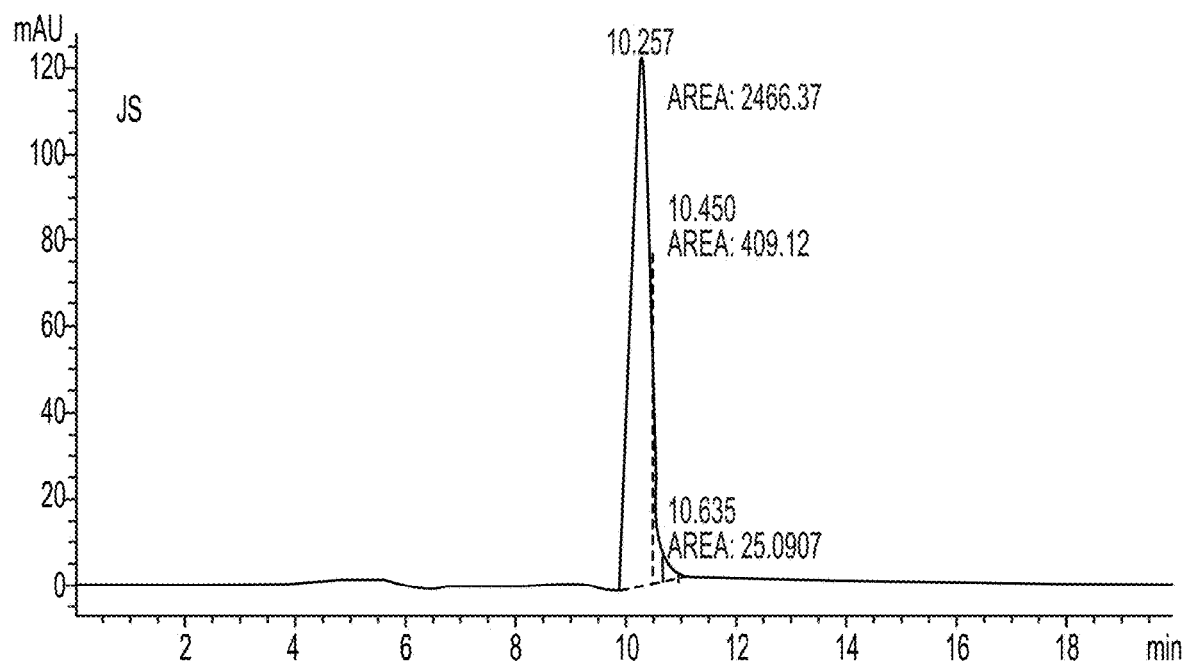
Figure 4C:
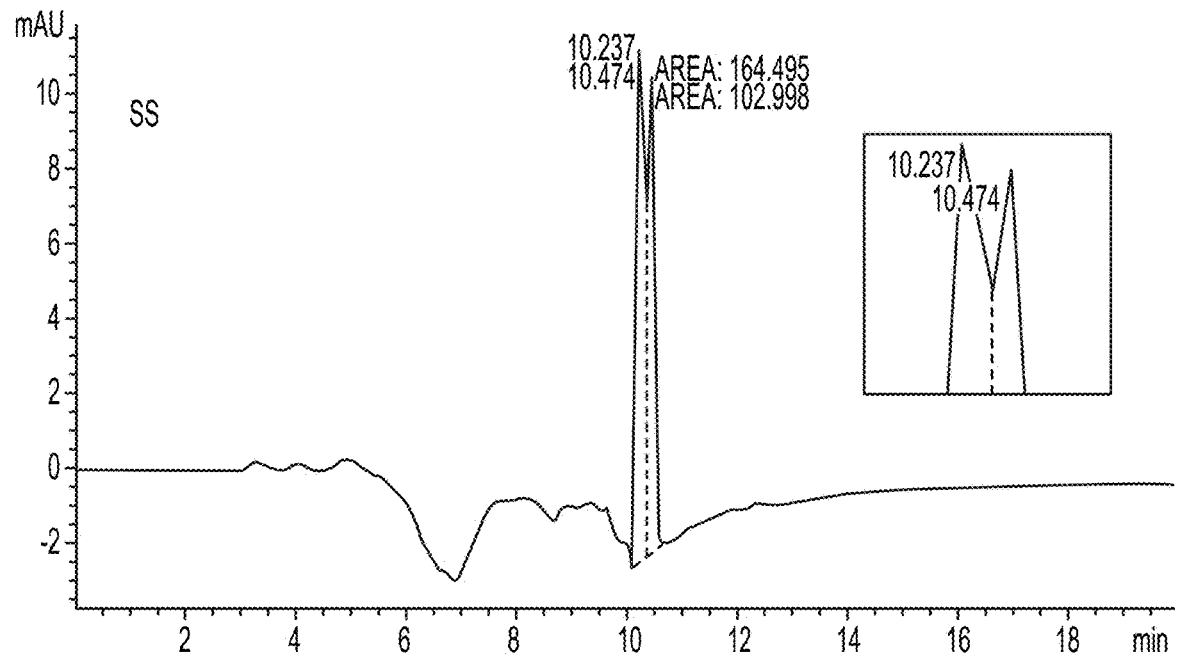
Figure 4D:
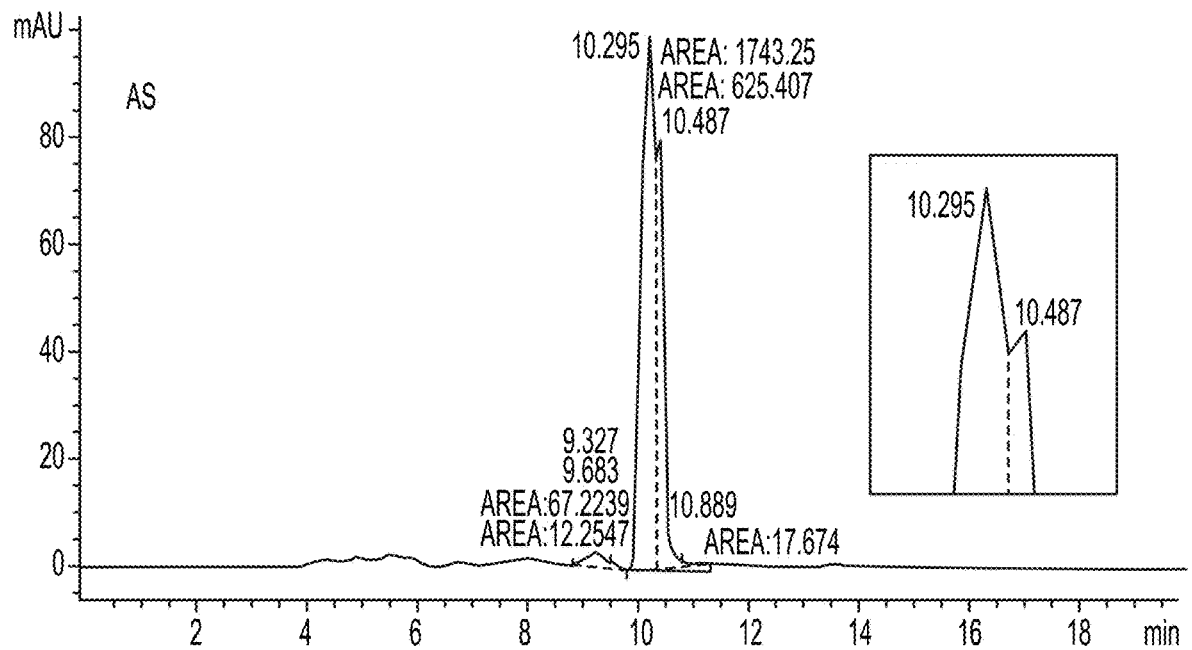

A size-exclusion chromatography (SEC) analysis of the four clones was performed, in part to identify the propensity for the scFvs to form soluble aggregates. As shown in FIG. 4A and FIG. 4B, the NS and JS clones display a single peak on SEC; thus, the NS and JS scFvs do not form aggregates in the conditions of the assay. On the other hand, as shown in FIG. 4C and FIG. 4D, the SS and AS clones display dual peaks on SEC; see, the insets in each figure. Thus, the SS and AS scFvs form an appreciable amount of soluble aggregates in the tested conditions.

CONCLUSION

In this example, anti-CD19 mouse monoclonal antibody (mAb) clone FMC63 was successfully humanized. Seven humanized scFvs were obtained from FASEBA high throughput screening and phage display technology. Four humanized scFvs (clones named SS, JS, AS, and NS) showed comparable binding (EC50 values) to the wild type FMC63 scFv.

Example 2: Characterization of Chimeric Antigen Receptors (CARs) Comprising Each Selected scFV Chimeric antigen receptors (CARs) were designed which express one of the four selected scFvs (SS, JS, AS, and NS) as its antigen binding molecule.

Thermo-Ramping Assay was Performed to Determine Thermostability of the Four scFvs Comprising the CAR Binding Domains Enhanced stability is a desired property of proteins. This is often assessed by determining the melting temperature of a protein under various conditions. Proteins with a higher melting temperature are generally stable for longer times. When a CAR is more thermostable, it may be functionally active for longer periods of time on the surface of a cell.

Thermal stability of the scFvs comprising the binding domains of the CARs of the present invention were measured using a Bio-Rad C1000 thermal cycler, CFx96 Real-Time system. Unfolding of the proteins was monitored using the fluorescent dye SYPRO® Orange (Invitrogen) which binds to hydrophobic amino acids that become exposed as the protein unfolds. A temperature gradient was set up from 25° C. to 95° C. with 1° C./minute stepwise increments. Each sample contained 10 µM of the CAR scFv and 5× SYPRO® Orange Protein Gel Stain (Molecular Probes™; 5,000× Concentrate in DMSO). 50 mM NaCl was included in the samples shown in FIG. 5A.

In this assay, an acceptable melting temperature for an CAR was ideally greater than 60° C.

Figure 5A:
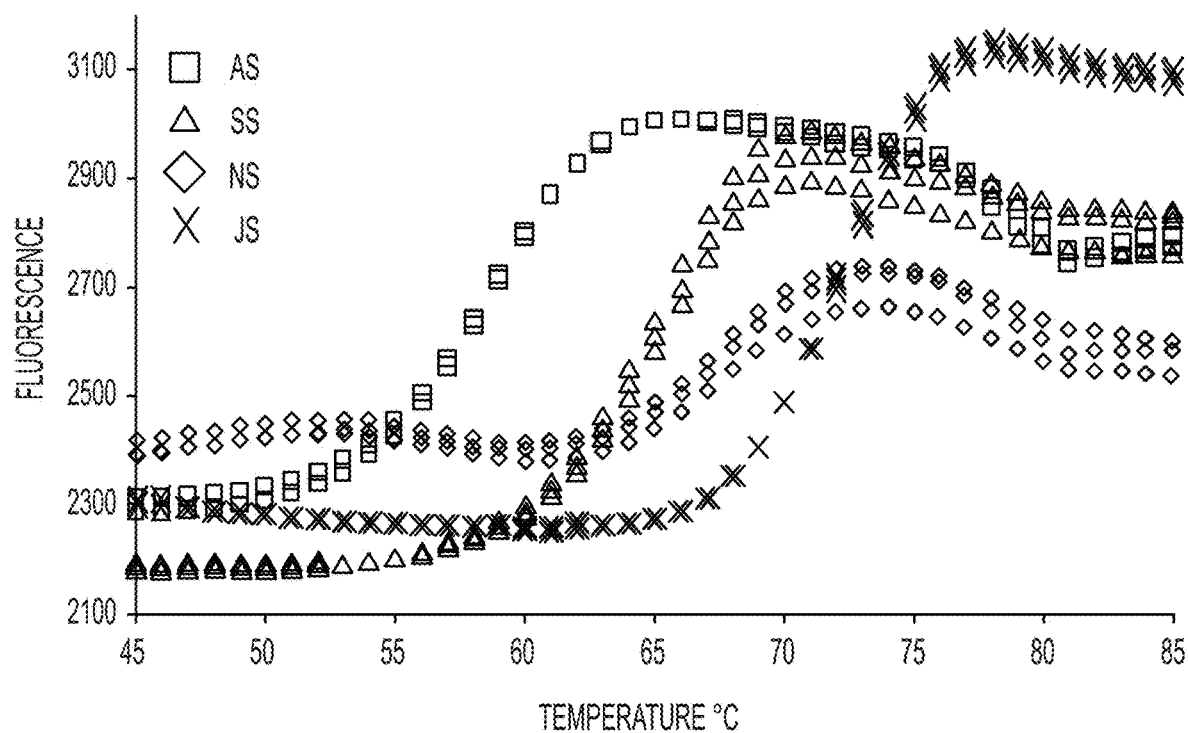
FIG. 5A and FIG. 5B are graphs showing thermal ramping to determine polypeptide stability of CARs comprising NS, SS, JS, and AS humanized scFvs.
Figure 5B:
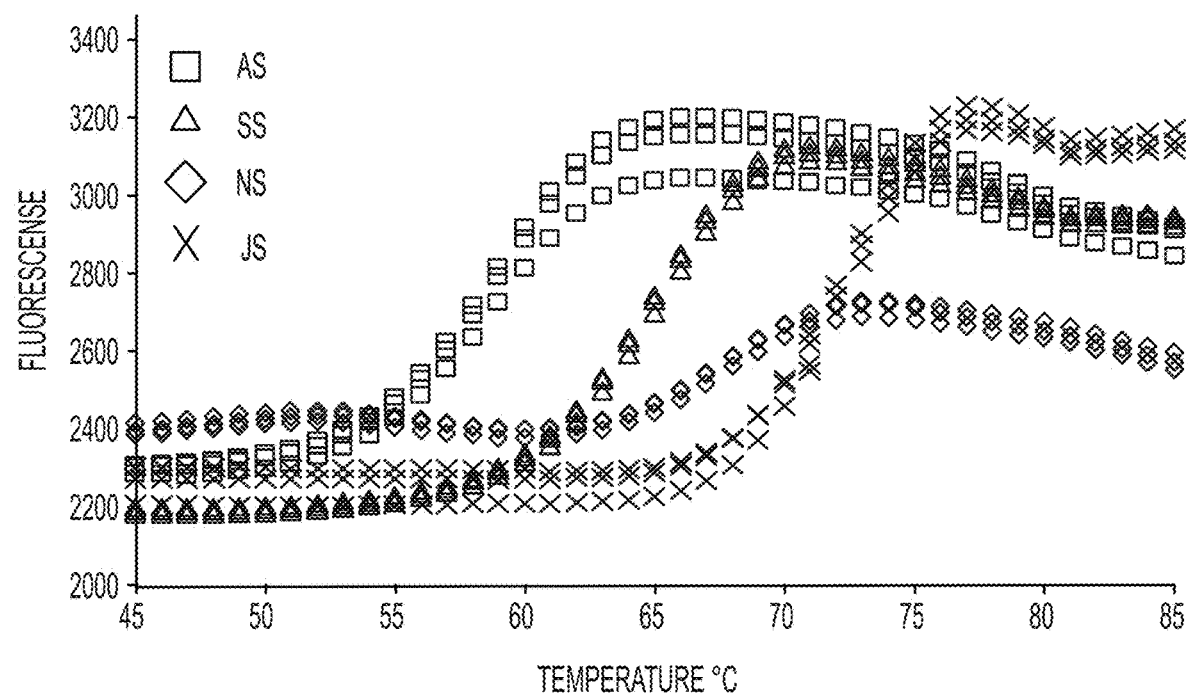

As shown in FIG. 5A, the CARs comprising humanized scFvs showed varied thermostabilities in the presence of 50 mM NaCl, with little difference when NaCl was omitted (as shown in FIG. 5B). Furthermore, the scFvs of the CARs of the present invention were quite stable relative to other-studied scFvs used in other CARs. AS ("☐") scFv had the lowest melting temperature of about 58° C.; increasing melting temperatures were seen for the scFVs of the SS clone ("Δ"; 65° C.), the JS clone ("◇"; 67° C.), and the NS clone ("X"; 73° C.).

CAR Expression in Two Cell Lines

The SS-, JS-, AS-, and NS-scFv-comprising CARs were expressed in two T cell donors' cells: 5244 (FIG. 6A) and 5273 (FIG. 6B) A mock-CAR expressing donor cell samples and donor cells expressing a CAR comprising the FMC63 (parental) scFV were also prepared.

CARs were detected on the surface of donor cells by incubating the cells with a PE-conjugated anti-CAR-antibody. The percentage CAR positive and fluorescence intensity was measured by flow cytometry.

Figure 6A:
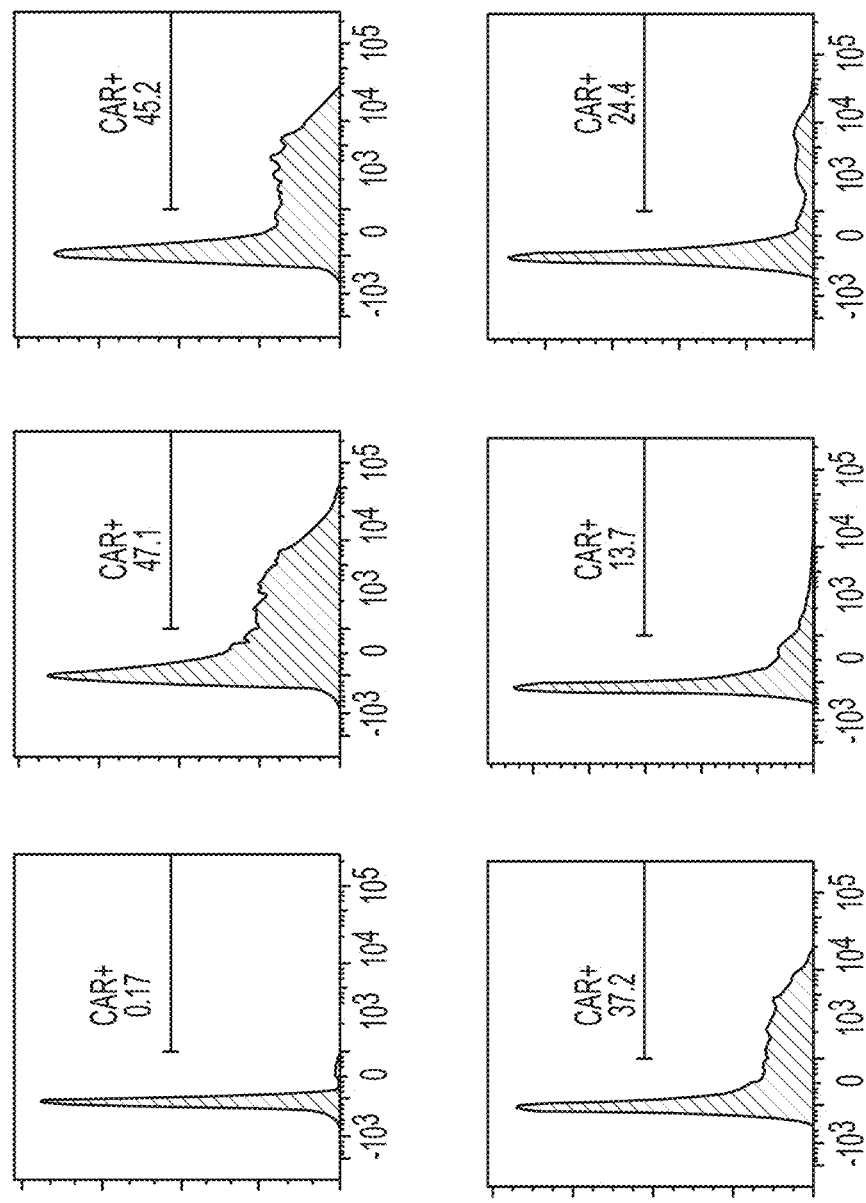
FIG. 6A and FIG. 6B include a series of plots showing detection of SS-, JS-, AS-, and NS-comprising CARs of the present invention expressed on the surface of T cells, which were obtained from two donor subjects 5244 (FIG. 6A) and 5273 (FIG. 6B). A mock-CAR expressing donor cells and donor cells expressing a CAR comprising the parental antibody ("FMC63") scFV were also prepared.
Figure 6B:
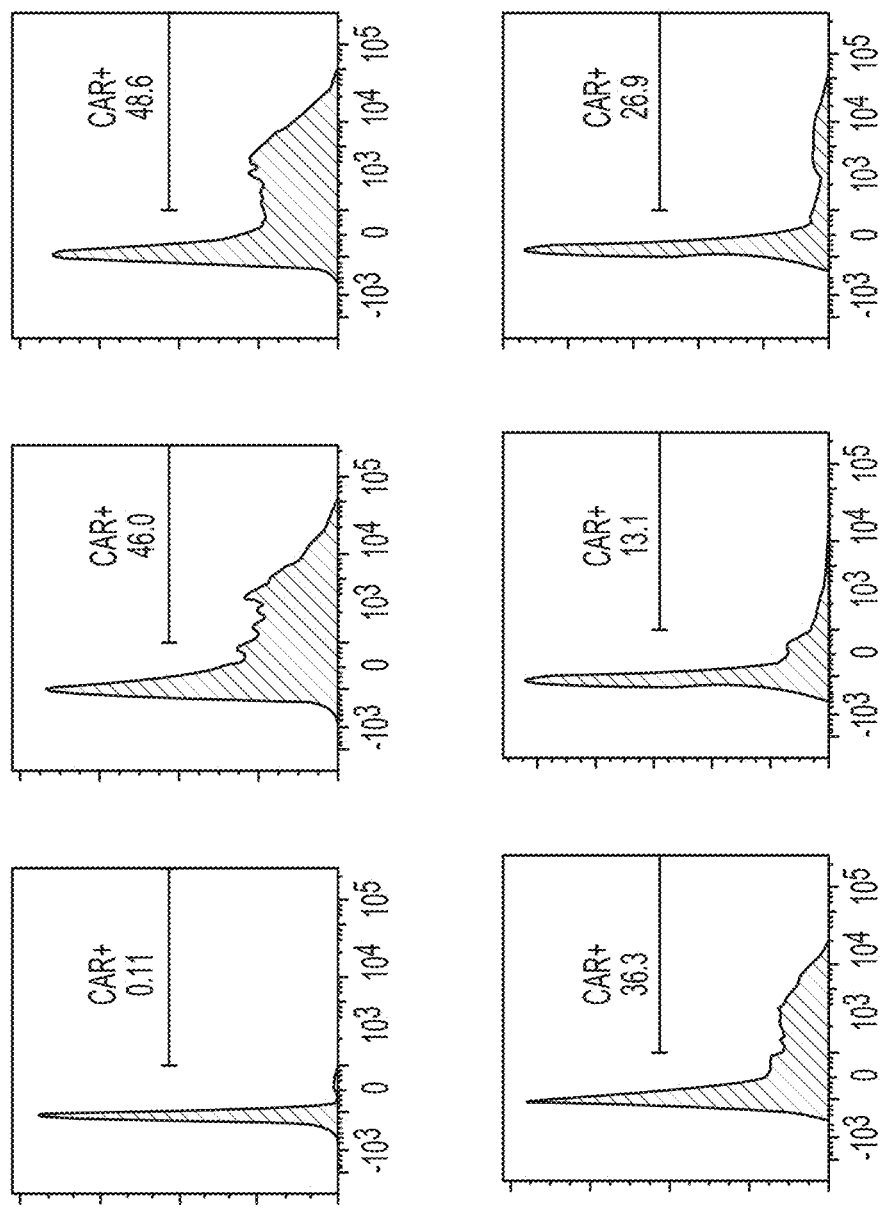

FIG. 6A and FIG. 6B show that no CAR was expressed in the Mock-transduced T cells. In cells of either donor, more SS CAR was expressed than the other three selected humanized scFv clones; the AS CAR had the least amount of expression.

Figure 7A:
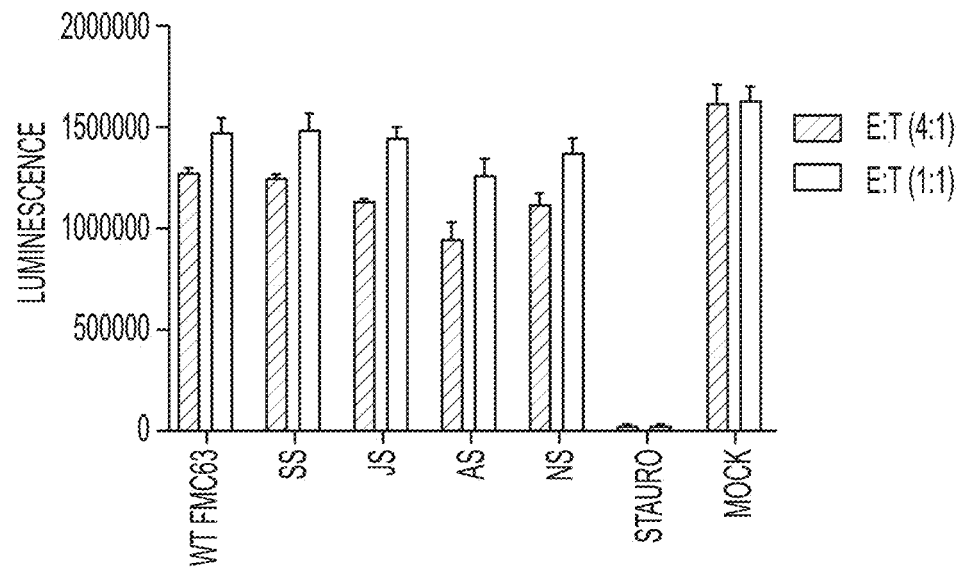
FIG. 7A to FIG. 7D include a series of bar graphs demonstrating cytolytic activity of CARs of the present invention with CAR- or mock-transduced donor cells from donor 5244. CAR- or mock-transduced donor cells were added at an effector to target ratio of 1:1 or 4:1. Four target cell types were used: Raji (CD19+*Homo sapiens* Burkitt's lymphoma cells.
Figure 7B:
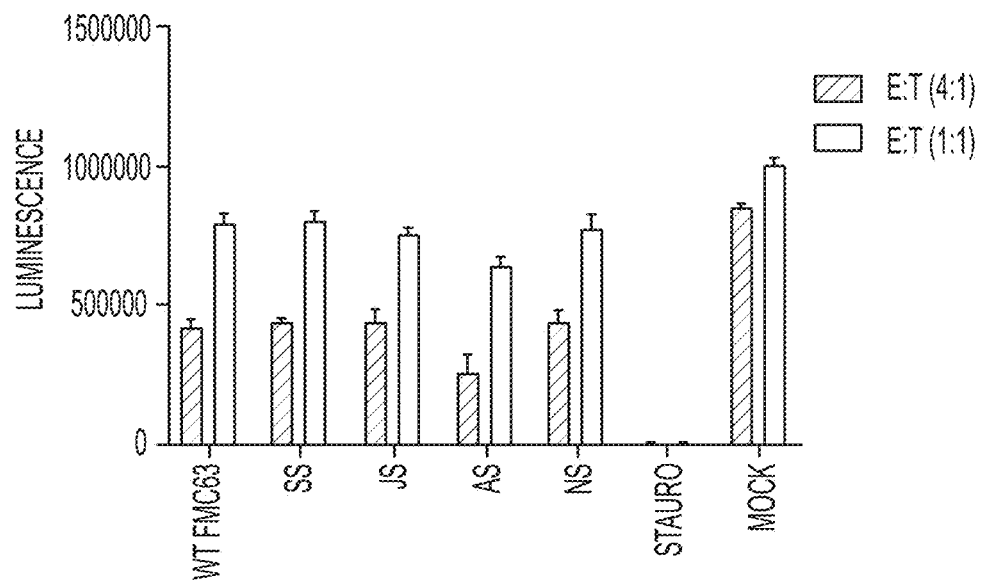
Figure 7C:
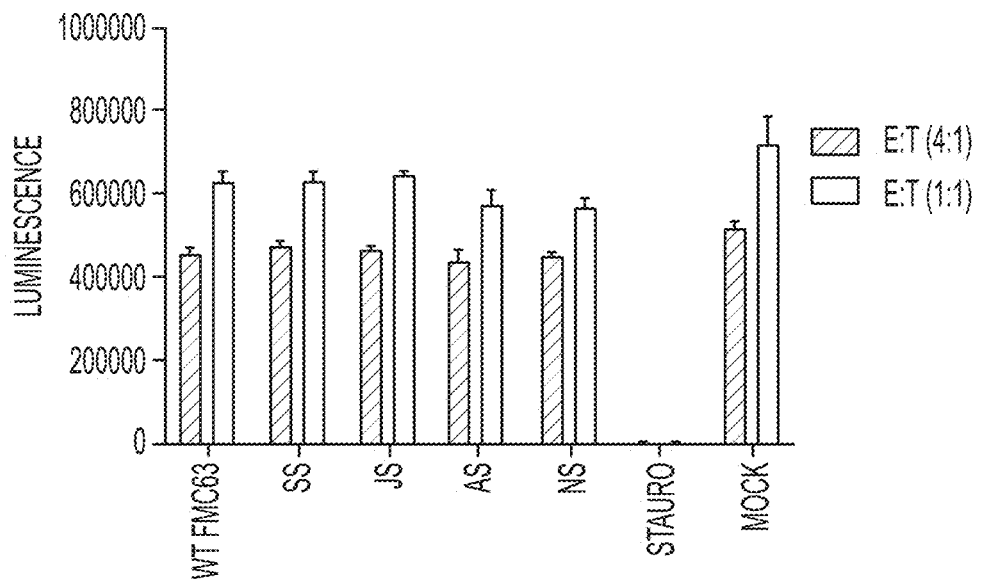
Figure 7D:
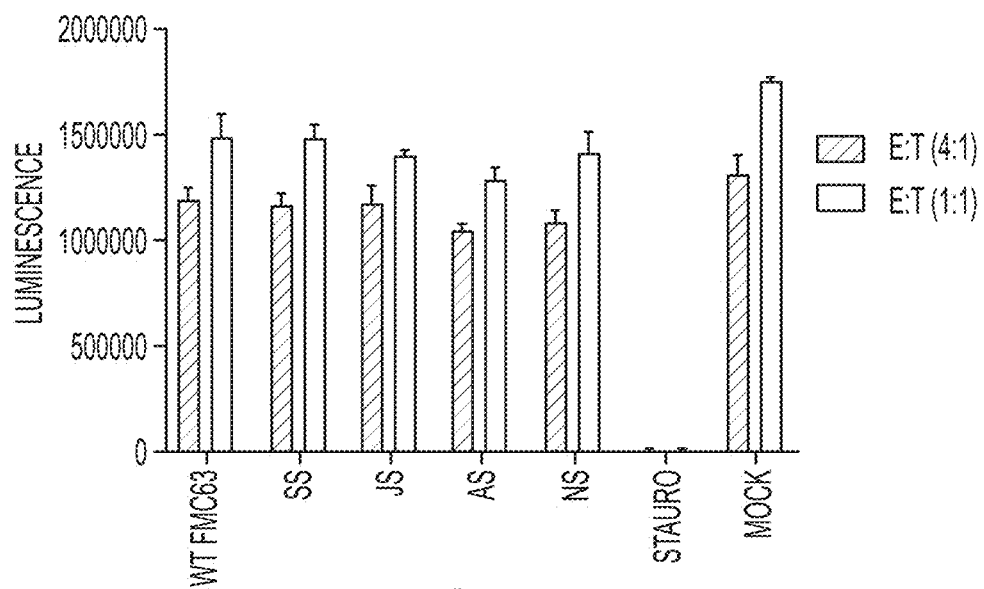
Figure 8A:
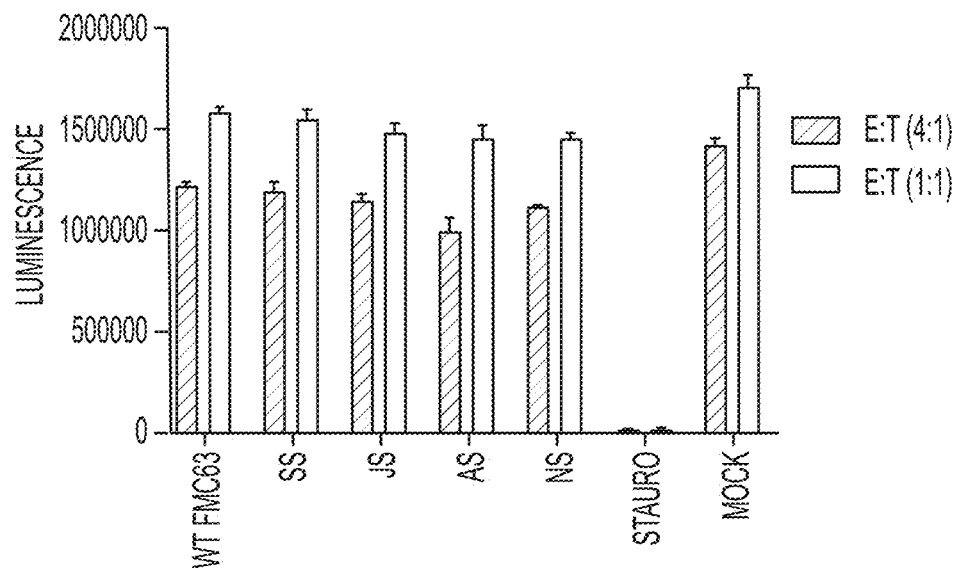
FIG. 8A to FIG. 8D include a series of bar graphs demonstrating cytolytic activity of CARs of the present invention with CAR- or mock-transduced donor cells from donor 5273.CAR- or mock-transduced donor cells were added at an effector to target ratio of 1:1 or 4:1 Four target cell types were used: Raji cells (FIG. 8A), Namalawa cells (FIG. 8B), Eol-1 cells (FIG. 8C), and Mv411 cells (FIG. 8D) were used. Stauro was used as a positive control for tumor cell killing.
Figure 8B:
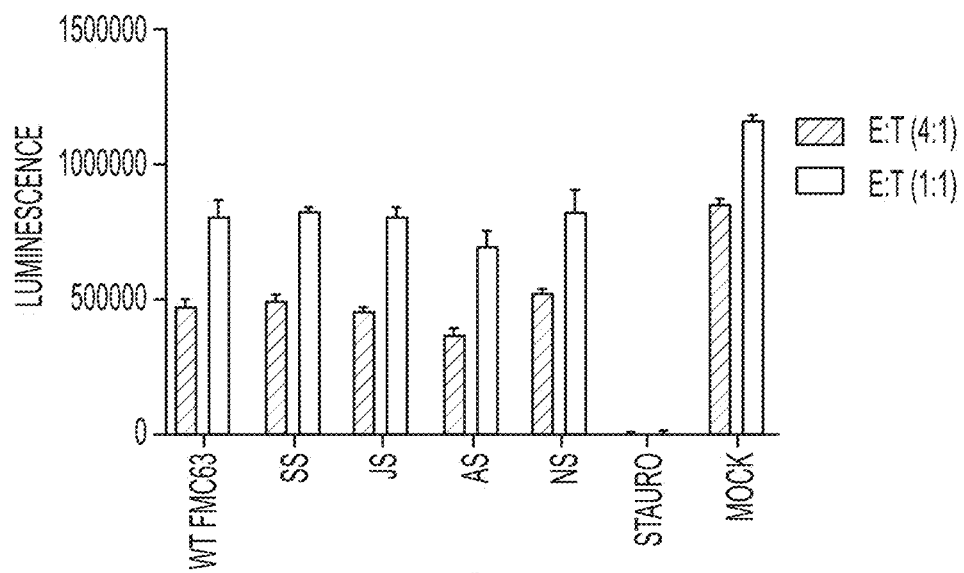
Figure 8C:
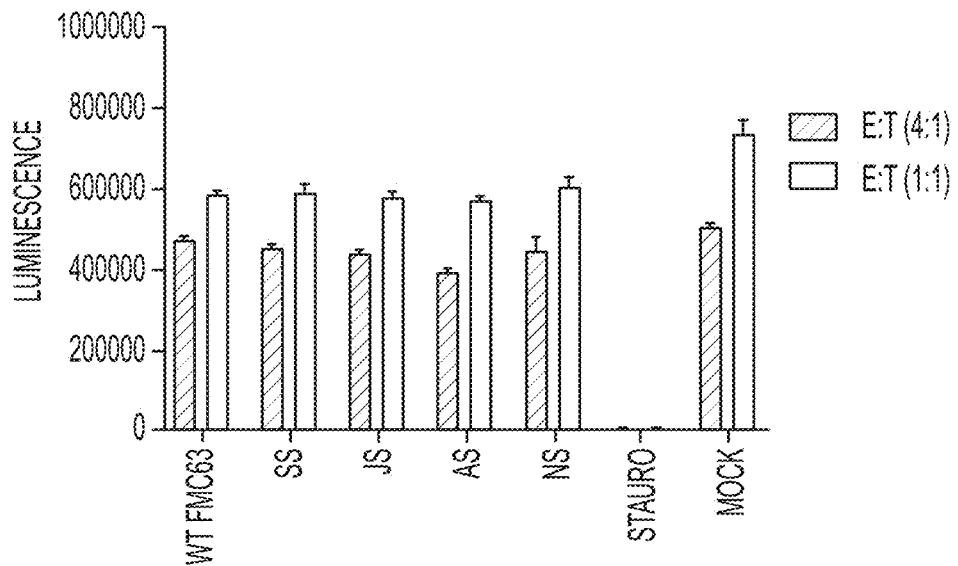
Figure 8D:
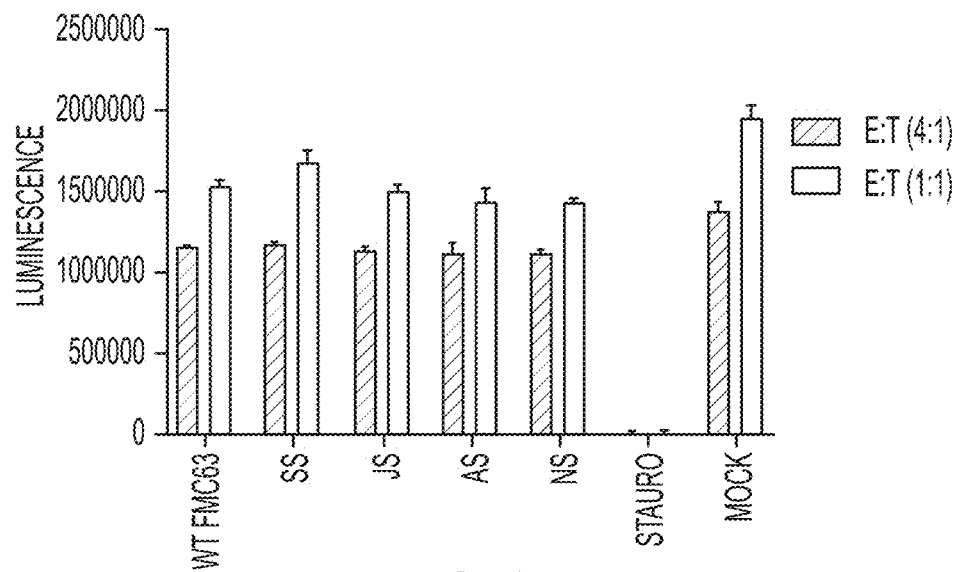

Example 3: CARs Comprising Each of the Selected scFVs Selectively Kills Tumor Cells CAR- or mock-transduced T cells from donor 5244 (FIG. 7A to 7D) or 5273 (FIGS. 8A to 8D) were added to target cell lines at an effector to target ratio of 1:1 or 4:1. Four target cell types were used: Raji (CD19+ Homo sapiens Burkitt's lymphoma cells; FIG. 7A and FIG. 8A), Namalawa (CD19+ Homo sapiens Burkitt's lymphoma cells; FIG. 7B and FIG. 8B), Eol-1 (CD19⁻ Homo sapiens acute myeloid (eosinophilic) leukemia cells; FIG. 7C and FIG. 8C), and Mv411 (CD19⁻ Homo sapiens biphenotypic B myelomonocytic leukemia cells; FIG. 7D and FIG. 8D). Staurosporine ("Stauro") was used as a positive control for tumor cell killing.

After co-culture for 18 hours at 37° C., 50 μL of steady-Glo luciferin reagent in R10 media was added to each well and plates were incubated at 37° C. for 10 minutes. Luciferase activity was used as a measure of cell viability. Luminescence was read in a Varioskan Flash plate reader.

FIGS. 7A-7D and 8A-8D show luminescence measured for the CAR-transduced donor cells and incubated with target cells. Each of the CARs of the present invention is capable of killing CD19+ target cells.

Figure 9A:
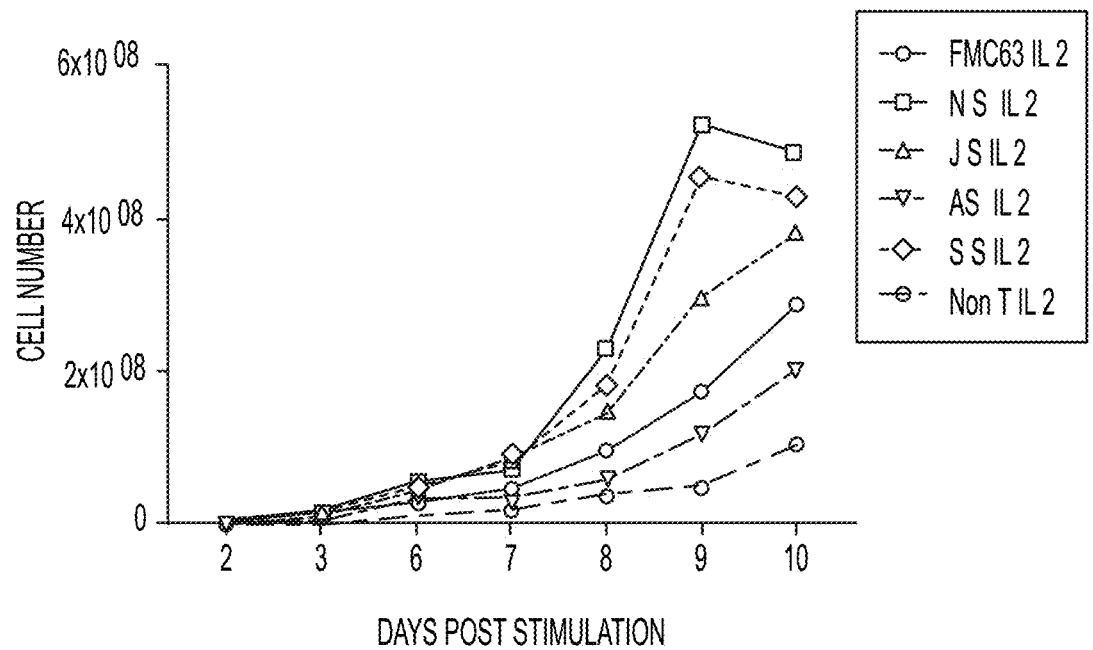
FIGS. 9A and 9B show the growth kinetics of CAR- or mock-transduced T cells from an additional donor measured over ten days after initial stimulation with OKT3. Observed growth profiles of each CAR are shown in FIG. 9A. CAR- or mock-transduced T cells were then stimulated a second time and differences in growth kinetics were observed as shown in FIG. 9B.
Figure 9B:
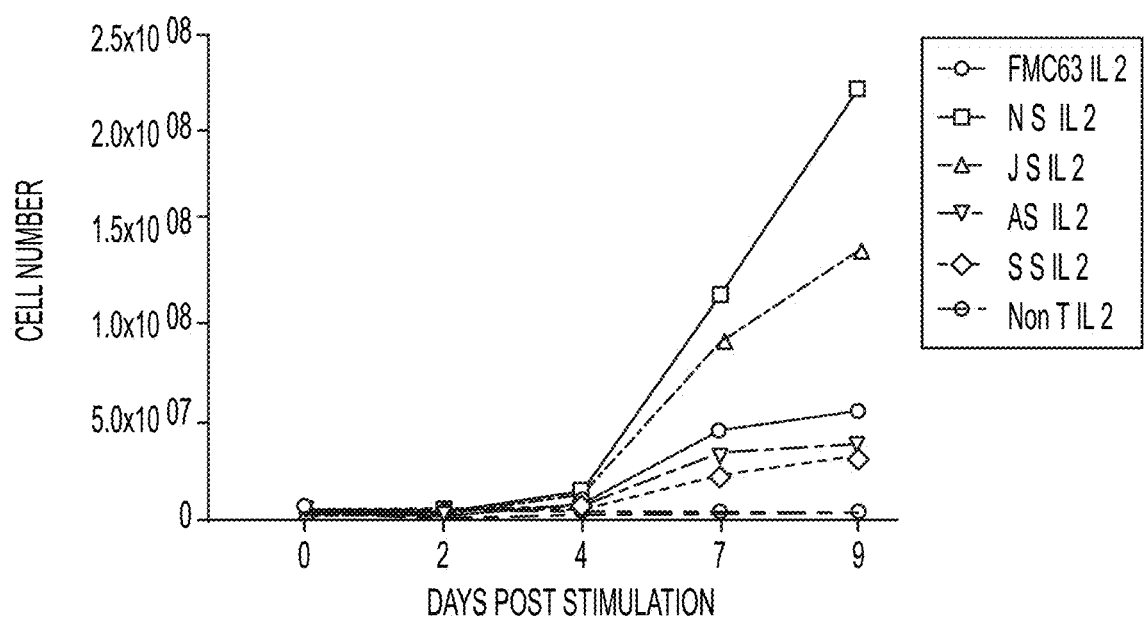
Figure 10A:
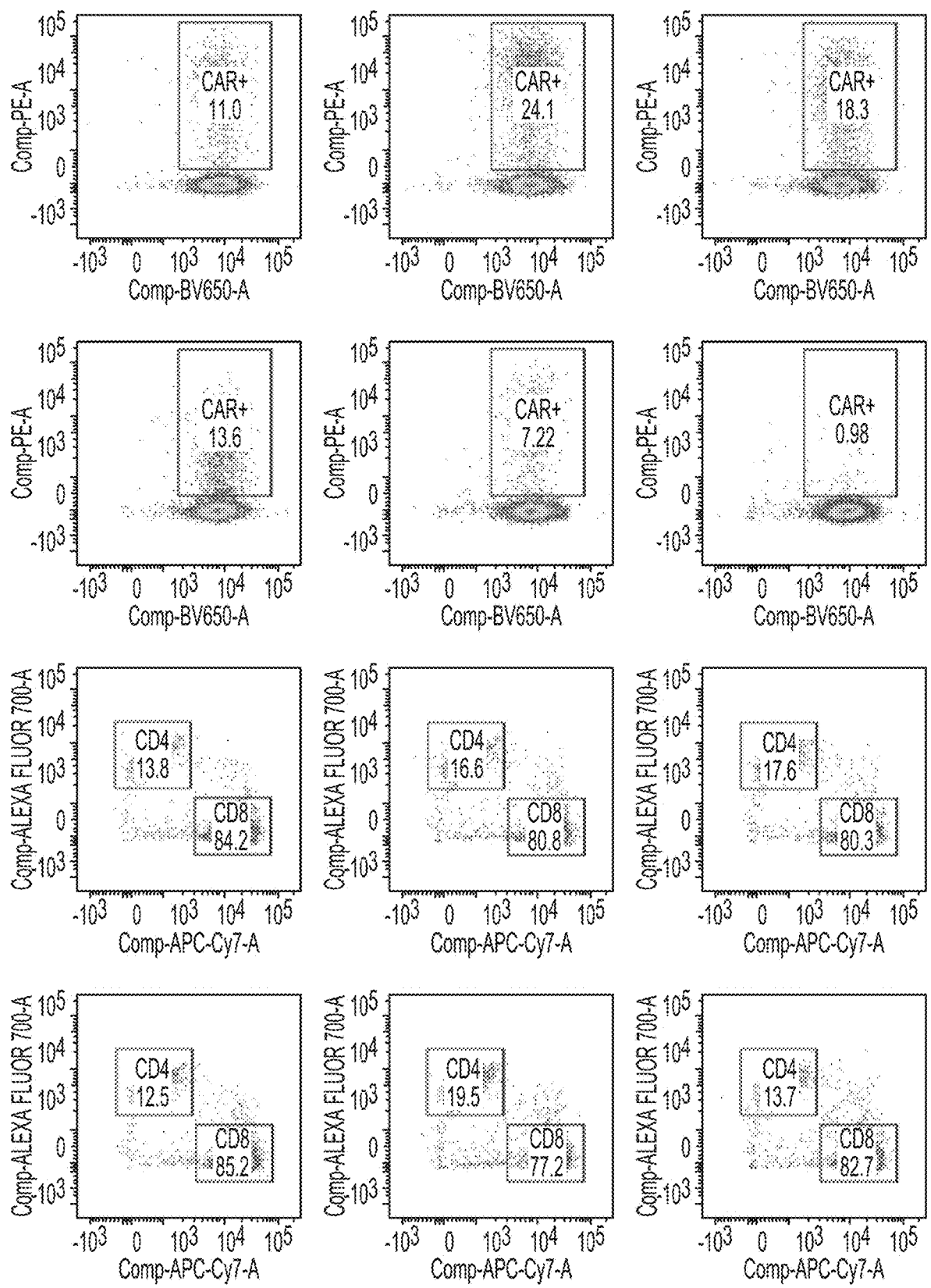
FIG. 10A shows the characterization of the T cell populations at day 10 using an anti-CAR antibody and CD3.
Figure 10B:
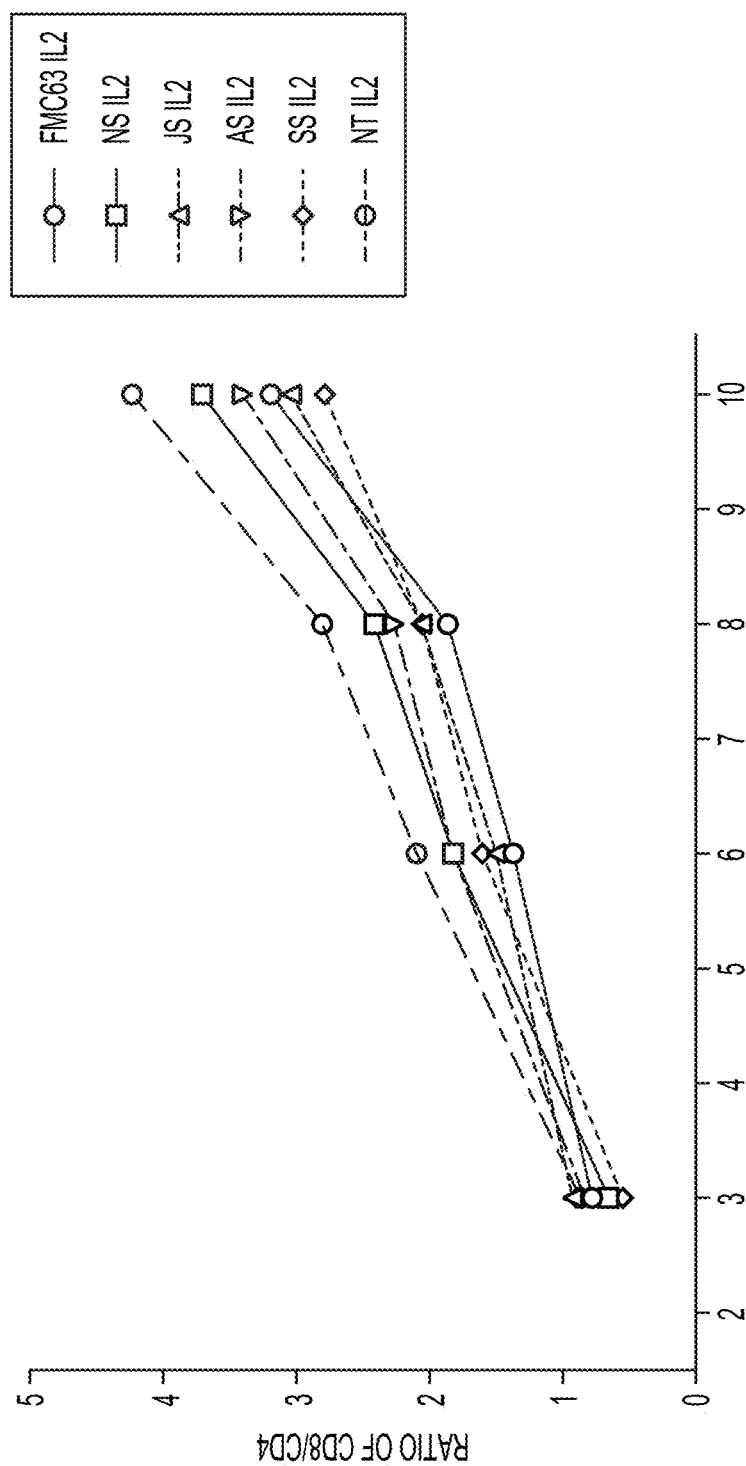
FIG. 10B shows CD4/CD8 staining during CAR T cell production.
Figure 11A:
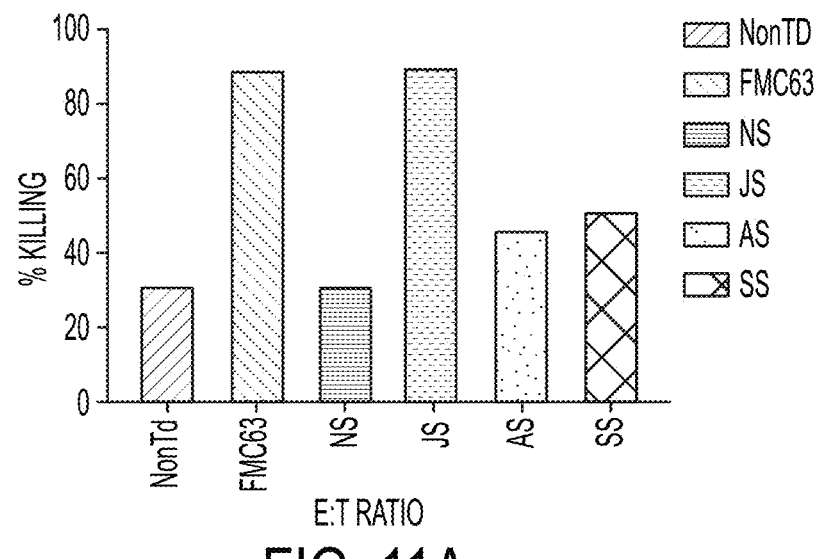
FIGS. 11A and 11B shows cytotoxicity assays performed on CD19+ NAMALWA (left panel) or CD19− EOL-1 (right panel) cells.
Figure 11B:
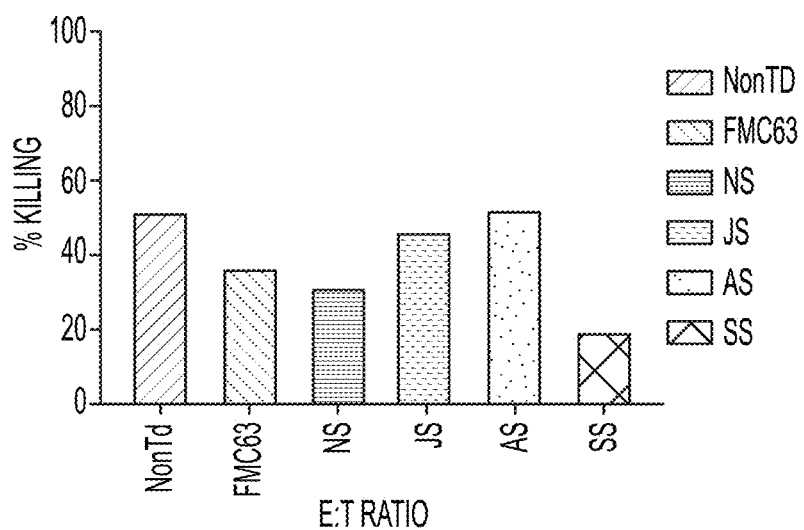

The growth kinetics of CAR- or mock-transduced T cells from an additional donor were measured over ten days after the initial stimulation with OKT3. Observed growth profiles of each CAR are shown in FIG. 9A. CAR- or mock-transduced T cells were then stimulated a second time and differences in growth kinetics were observed as shown in FIG. 9B. At day 10, characterization of the T cell populations were undertaken with an anti-CAR antibody and CD3 (FIG. 10A). CD4/CD8 staining was also performed to monitor enrichment of CD8 cells during CAR T cell production shown in FIG. 10B. Cytotoxicity assays were performed on CD19+ NAMALWA (FIG. 11A) or CD19−EOL-1 (FIG. 11B) at an effector to target ratio of 1:1.

What is claimed is:

1. A humanized anti-CD19 antibody or antigen binding fragment thereof comprising a light chain variable (VL) region and a heavy chain variable (VH) region, wherein the VL region comprises a VL complementarity determining region (CDR) 1 (VL CDRI), a VL CDR2, and a VL CDR3 and the VH region comprises a VH CDRI, a VH CDR2, and a VH CDR3,
   wherein the VL region has an amino acid sequence at least 95% identical to SEQ ID NO: 14, SEQ ID NO: 20, SEQ ID NO: 11, or SEQ ID NO: 17;
   wherein the VH region has an amino acid sequence at least 95% identical to SEQ ID NO: 15, SEQ ID NO: 21, SEQ ID NO: 12, or SEQ ID NO: 18;
   wherein the VL CDRI is SEQ ID NO: 27, the VL CDR2 is SEQ ID NO: 28, and the VL CDR3 is SEQ ID NO: 29; and
   wherein the VH CDRI is SEQ ID NO: 30 or 33, the VH CDR2 is SEQ ID NO: 31 or 34, and the VH CDR3 is SEQ ID NO: 32.

2. The humanized anti-CD19 antibody or antigen binding fragment thereof of claim 1, wherein the antibody or the antigen binding fragment thereof is selected from the group consisting of an IgG, an Fab, an Fab', an F(ab')$_2$, an Fv, and an scFv.

3. A polypeptide comprising the humanized anti-CD19 antibody or antigen binding fragment thereof of claim 1.

4. A chimeric antigen receptor (CAR) or a T cell receptor (TCR), comprising: (i) an antigen binding domain, (ii) a costimulatory domain, and (iii) an activating domain,
   wherein the costimulatory domain comprises an extracellular domain, a transmembrane domain, and an intracellular domain, and
   wherein the antigen binding domain comprises at least the polypeptide of claim 3.

5. The CAR or TCR of claim 4, wherein the costimulatory domain is from or is derived from CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1 BB), CD150

(SLAMF1), CD158A (KIR2DL1), CD158B1 (KIR2DL2), CD158B2 (KIR2DL3), CD158C (KIR3DP1), CD158D (KIRDL4), CD158FI (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class I molecule, MHC class 2 molecule, a TNF receptor protein, an immunoglobulin protein, a cytokine receptor, an integrin, activating NK cell receptors, a Toll ligand receptor, and fragments or combinations thereof.

6. The CAR or TCR of claim 4, wherein the transmembrane domain is from or is derived from 4-1BB/CD137, an alpha chain of a T cell receptor, a beta chain of a T cell receptor, CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1 BB), CD150 (SLAMF1), CD158A (KIR2DL1), CD158B1 (KIR2DL2), CD158B2 (KIR2DL3), CD158C (KIR3DP1), CD158D (KIRDL4), CD158FI (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class I molecule, MHC class 2 molecule, a TNF receptor protein, an immunoglobulin protein, a cytokine receptor, an integrin, activating NK cell receptors, a Toll ligand receptor, and combinations thereof.

7. The CAR or TCR of claim 4, wherein the intracellular domain is from or is derived from 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-I (LFA-1 (CD11a/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, or VLA-6, or a combination thereof.

8. The CAR or TCR of claim 4, wherein the extracellular domain is from or is derived from CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1 BB), CD150 (SLAMF1), CD158A (KIR2DL1), CD158B1 (KIR2DL2), CD158B2 (KIR2DL3), CD158C (KIR3DP1), CD158D (KIRDL4), CD158FI (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof.

9. The CAR or TCR of claim 4, wherein the activating domain is from or is derived from CD3-zeta or CD3-episilon.

10. A vector comprising the humanized anti-CD19 antibody or antigen binding fragment thereof of encoding the CAR or TCR of claim 4.

11. A cell comprising a chimeric antigen receptor (CAR) or T cell receptor (TCR) of claim 4.

12. A composition comprising a plurality of cells of claim 11.

13. A method for manufacturing a cell expressing a chimeric antigen receptor (CAR) or a T cell receptor (TCR), comprising a step of transducing a cell with a vector of claim 10.

14. A method for treating a B-cell lymphoma comprising administering to a subject in need thereof a cell of a composition of claim 12.

15. The method of claim 14, wherein the B-cell lymphoma is selected from the group consisting of Acute Lymphoblastic Leukemia (ALL), AIDS-related lymphoma, ALK-positive large B-cell lymphoma, Burkitt's lymphoma, Chronic lymphocytic leukemia, CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia.

* * * * *

UNITED STATES PATENT AND TRADEMARK OFFICE
CERTIFICATE OF CORRECTION

PATENT NO. : 10,844,120 B2  
APPLICATION NO. : 15/961562  
DATED : November 24, 2020  
INVENTOR(S) : Jed J. W. Wiltzius et al.

Page 1 of 1

It is certified that error appears in the above-identified patent and that said Letters Patent is hereby corrected as shown below:

In the Claims

In Claim 1, Column 85, Line 48, please delete "(VL CDRI)" and insert in place thereof —(VL CDR1)—
In Claim 1, Column 85, Line 49, please delete "VH CDRI" and insert in place thereof —VH CDR1—
In Claim 1, Column 85, Line 57, please delete "VL CDRI" and insert in place thereof —VL CDR1—
In Claim 1, Column 85, Line 60, please delete "VH CDRI" and insert in place thereof —VH CDR1—
In Claim 5, Column 86, Line 67, please delete "(4-1 BB)" and insert in place thereof —(4-1BB)—
In Claim 5, Column 87, Line 3, please delete "CD158FI" and insert in place thereof —CD158F1—
In Claim 6, Column 87, Line 35, please delete "(4-1 BB)" and insert in place thereof —(4-1BB)—
In Claim 6, Column 87, Line 37, please delete "CD158FI" and insert in place thereof —CD158F1—
In Claim 8, Column 88, Line 27, please delete "(4-1 BB)" and insert in place thereof —(4-1BB)—
In Claim 8, Column 88, Line 30, please delete "CD158FI" and insert in place thereof —CD158F1—

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*